US009888832B2

(12) United States Patent
Schwartz et al.

(10) Patent No.: US 9,888,832 B2
(45) Date of Patent: Feb. 13, 2018

(54) ENDOTRACHEAL INTUBATION DEVICE

(75) Inventors: John Schwartz, Williamston, MI (US); Richard Schwartz, Evans, GA (US); Harsha Setty, Martinez, GA (US)

(73) Assignee: Blink Device LLC, Seattle, WA (US)

( * ) Notice: Subject to any disclaimer, the term of this patent is extended or adjusted under 35 U.S.C. 154(b) by 394 days.

(21) Appl. No.: 12/924,358

(22) Filed: Sep. 24, 2010

(65) Prior Publication Data

US 2012/0078050 A1    Mar. 29, 2012

(51) Int. Cl.
| | | |
|---|---|---|
| *A61B 1/00* | (2006.01) | |
| *A61B 1/005* | (2006.01) | |
| *A61B 1/267* | (2006.01) | |
| *A61M 25/01* | (2006.01) | |
| *A61M 25/04* | (2006.01) | |
| *A61M 16/04* | (2006.01) | |
| *A61B 1/05* | (2006.01) | |

(52) U.S. Cl.
CPC ........ *A61B 1/00052* (2013.01); *A61B 1/0051* (2013.01); *A61B 1/0052* (2013.01); *A61B 1/0057* (2013.01); *A61B 1/00105* (2013.01); *A61B 1/267* (2013.01); *A61M 16/0488* (2013.01); *A61M 25/0136* (2013.01); *A61M 25/04* (2013.01); *A61B 1/05* (2013.01); *A61B 1/2673* (2013.01); *A61B 1/2676* (2013.01)

(58) Field of Classification Search
CPC .................. A61B 1/0055; A61B 1/267; A61B 1/0051–1/0053; A61B 1/0056; A61B 1/00105; A61B 1/00128; A61B 1/0057; A61B 1/2673; A61B 1/2676; A61M 25/0136; A61M 25/04

USPC ...... 600/120, 136, 140, 146–151; 604/95.04, 604/95.05
See application file for complete search history.

(56) References Cited

U.S. PATENT DOCUMENTS

| | | |
|---|---|---|
| 2,975,785 A | 3/1961 | Sheldon |
| 3,162,214 A | 12/1964 | Bazinet, Jr. |
| (Continued) | | |

FOREIGN PATENT DOCUMENTS

| | | | |
|---|---|---|---|
| JP | 5329095 | 12/1993 | |
| JP | 2005-046273 A | * 2/2005 | ............... A61B 1/00 |

OTHER PUBLICATIONS

International Search Report and Written Opinion of the International Searching Authority for PCT/US2009/005622, completed Dec. 18, 2009.

*Primary Examiner* — Timothy J Neal
*Assistant Examiner* — Aaron B Fairchild
(74) *Attorney, Agent, or Firm* — Brooks Kushman P.C.

(57) ABSTRACT

A stylet assembly for performing a nasal endotracheal intubation of a patient is disclosed. The stylet assembly includes an elongated tube as a stylet for the intubation defining a longitudinal axis, a proximal end, and a distal end for entering the trachea of the patient. The elongated tube includes (i) a rigid section adjacent the proximal end, (ii) an articulation section adjacent the distal end and adapted to curve into the patient's trachea upon actuation, and (iii) a flexible section between the rigid section and the articulation section, the flexible section being adapted to curve to an internal shape of at least one of the patient's nose, nasal cavity, pharynx, and larynx during nasal intubation. The stylet assembly can further include an actuator housing, a control wire for actuating the articulating section, and a hand grip for maneuvering the stylet assembly.

28 Claims, 33 Drawing Sheets

(56) References Cited

U.S. PATENT DOCUMENTS

| | | | |
|---|---|---|---|
| 3,913,568 A * | 10/1975 | Carpenter | 600/142 |
| 4,236,509 A | 12/1980 | Takahashi et al. | |
| 4,669,172 A | 6/1987 | Petruzzi | |
| 4,846,153 A | 7/1989 | Berci | |
| 4,877,016 A | 10/1989 | Kantor et al. | |
| 4,905,666 A | 3/1990 | Fukuda | |
| 4,919,112 A * | 4/1990 | Siegmund | 600/136 |
| 4,949,716 A | 8/1990 | Chenoweth | |
| 5,158,086 A * | 10/1992 | Brown | A61B 1/0057 600/152 |
| 5,520,222 A | 5/1996 | Chikama | |
| 5,549,542 A * | 8/1996 | Kovalcheck | A61B 1/0052 600/146 |
| 6,338,657 B1 * | 1/2002 | Harper et al. | 439/692 |
| 6,539,942 B2 | 4/2003 | Schwartz et al. | |
| 7,458,375 B2 | 12/2008 | Schwartz et al. | |
| 7,658,708 B2 | 2/2010 | Schwartz et al. | |
| 2002/0045803 A1 * | 4/2002 | Abe | A61B 1/0055 600/140 |
| 2003/0212308 A1 * | 11/2003 | Bendall | A61B 1/00052 600/131 |
| 2005/0039754 A1 | 2/2005 | Simon | |
| 2006/0004258 A1 | 1/2006 | Sun et al. | |
| 2007/0162095 A1 | 7/2007 | Kimmel et al. | |
| 2008/0200758 A1 | 8/2008 | Orbay et al. | |
| 2008/0200761 A1 * | 8/2008 | Schwartz et al. | 600/120 |
| 2008/0208000 A1 | 8/2008 | Schwartz et al. | |
| 2008/0308098 A1 | 12/2008 | Schwartz et al. | |
| 2009/0090357 A1 | 4/2009 | Schwartz et al. | |
| 2010/0095969 A1 | 4/2010 | Schwartz et al. | |
| 2010/0160730 A1 * | 6/2010 | Konomura | A61B 1/0057 600/146 |

\* cited by examiner

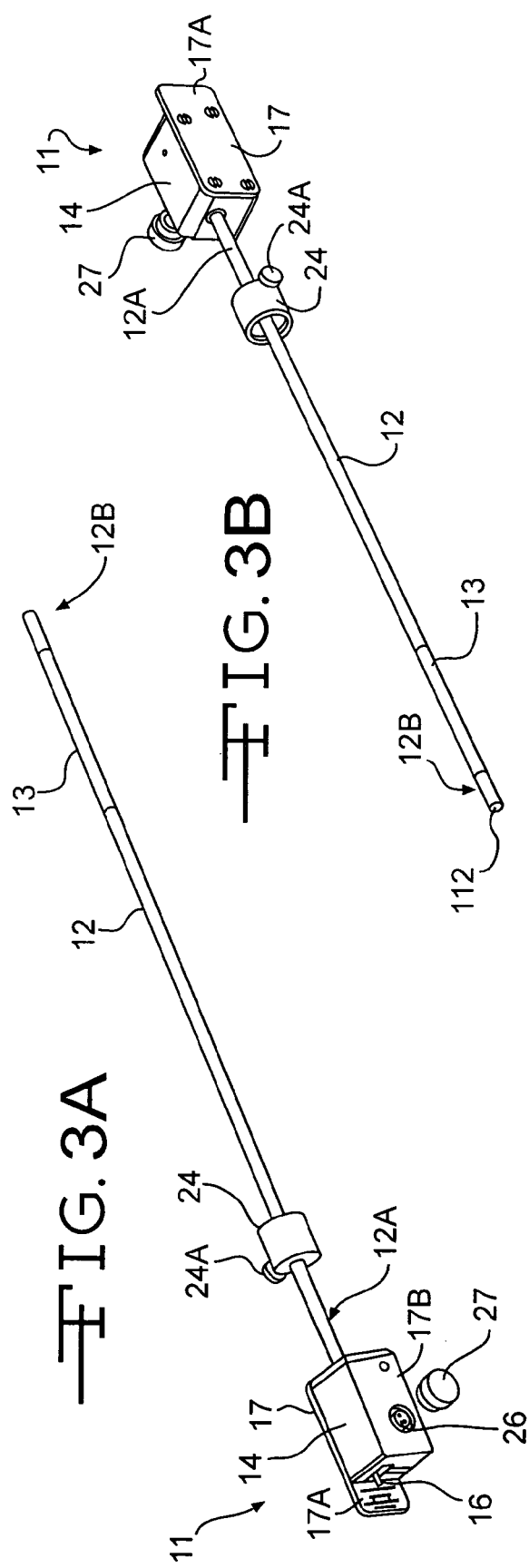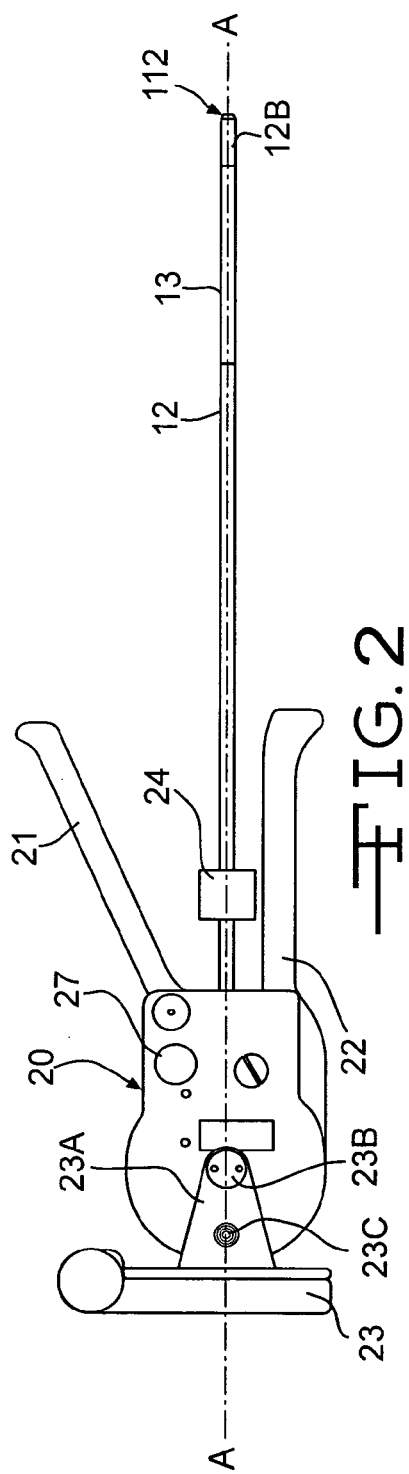

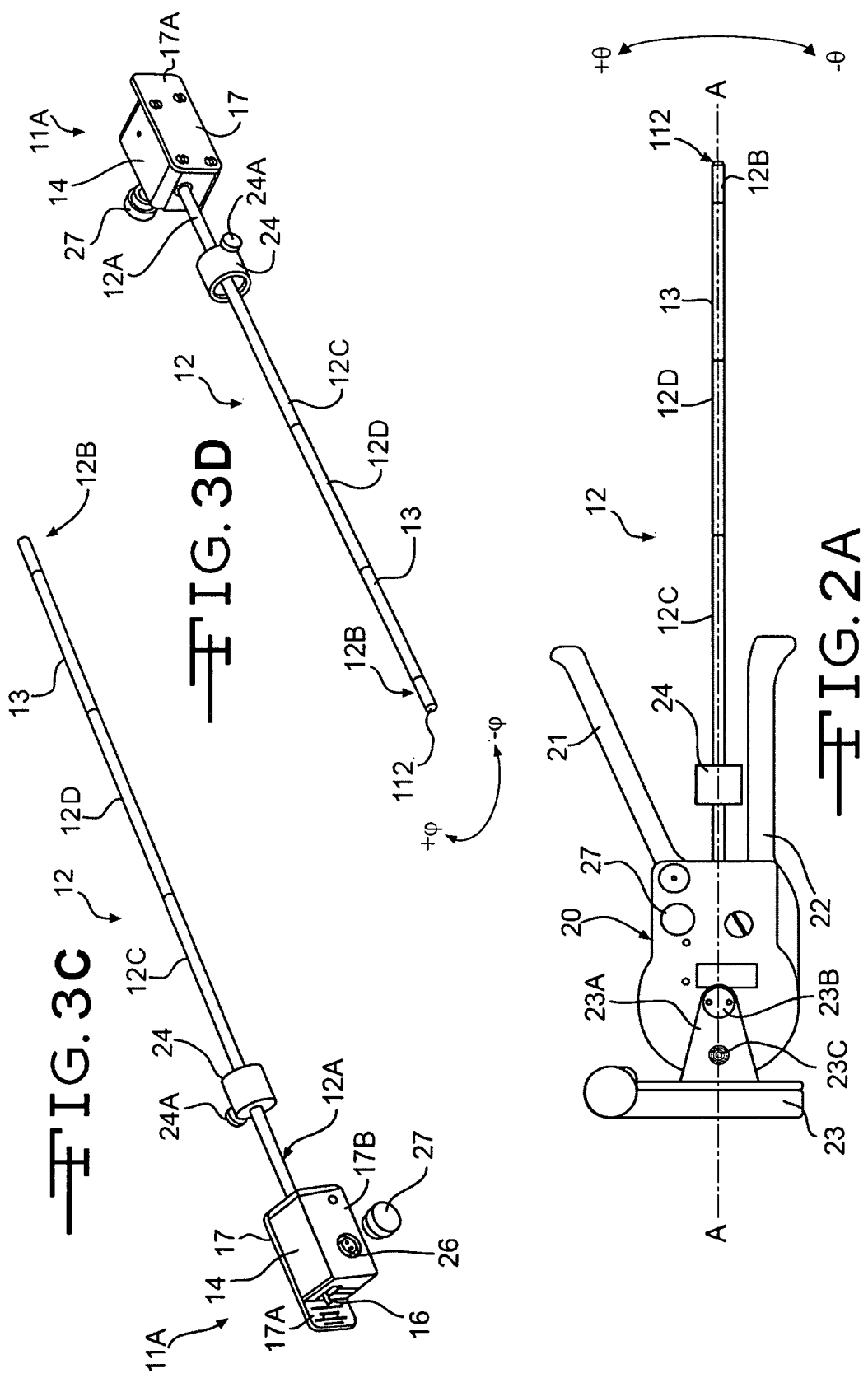

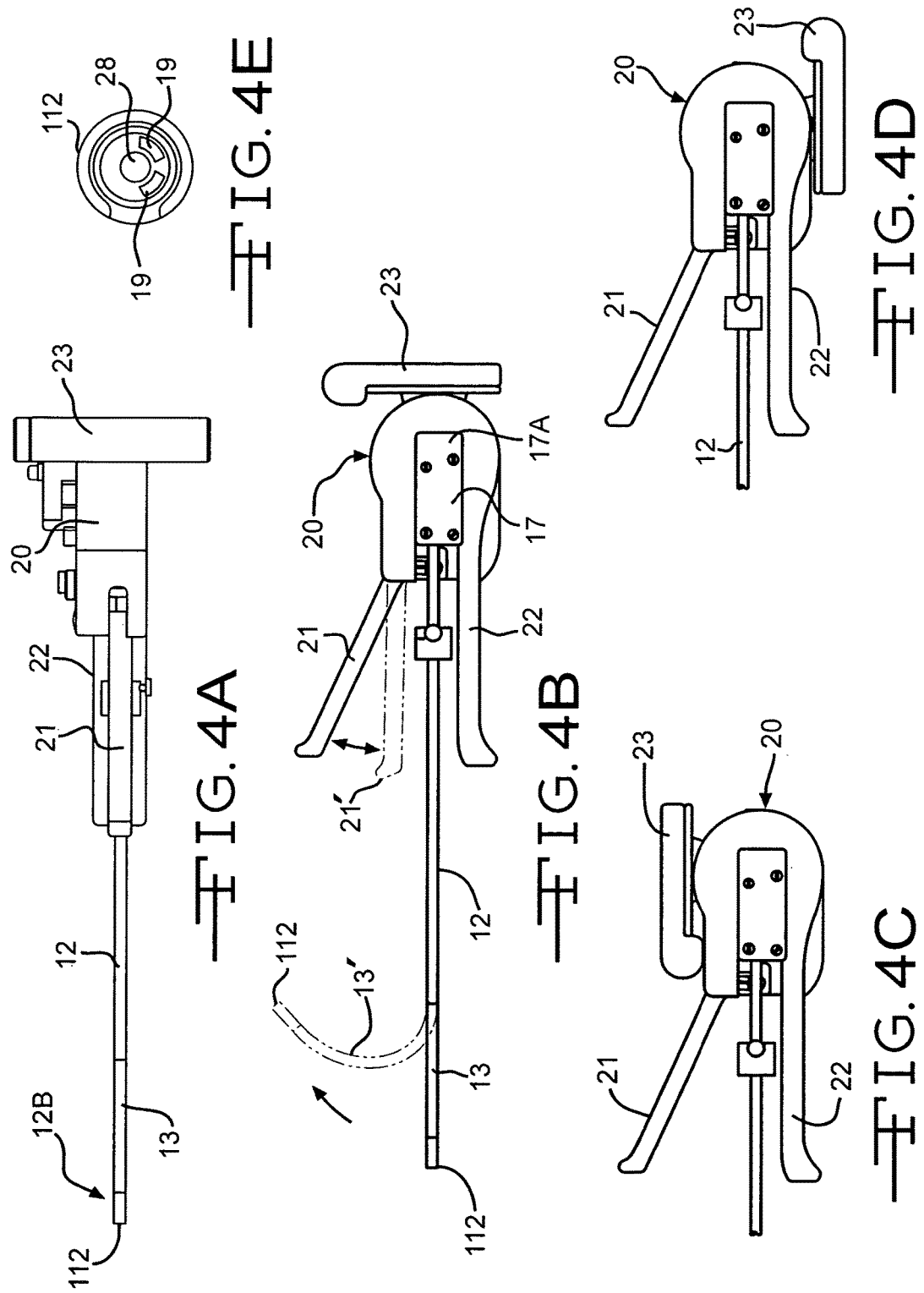

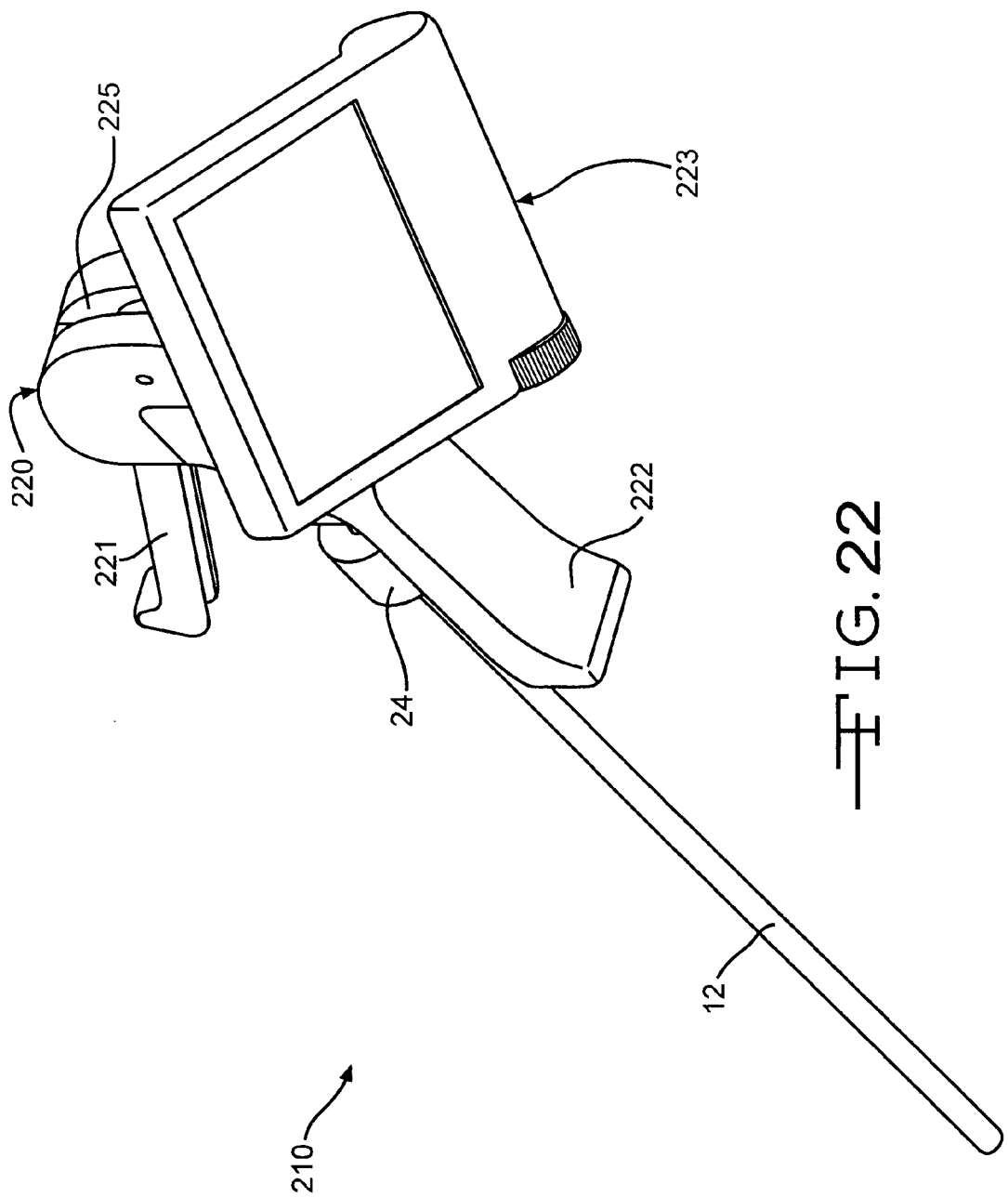

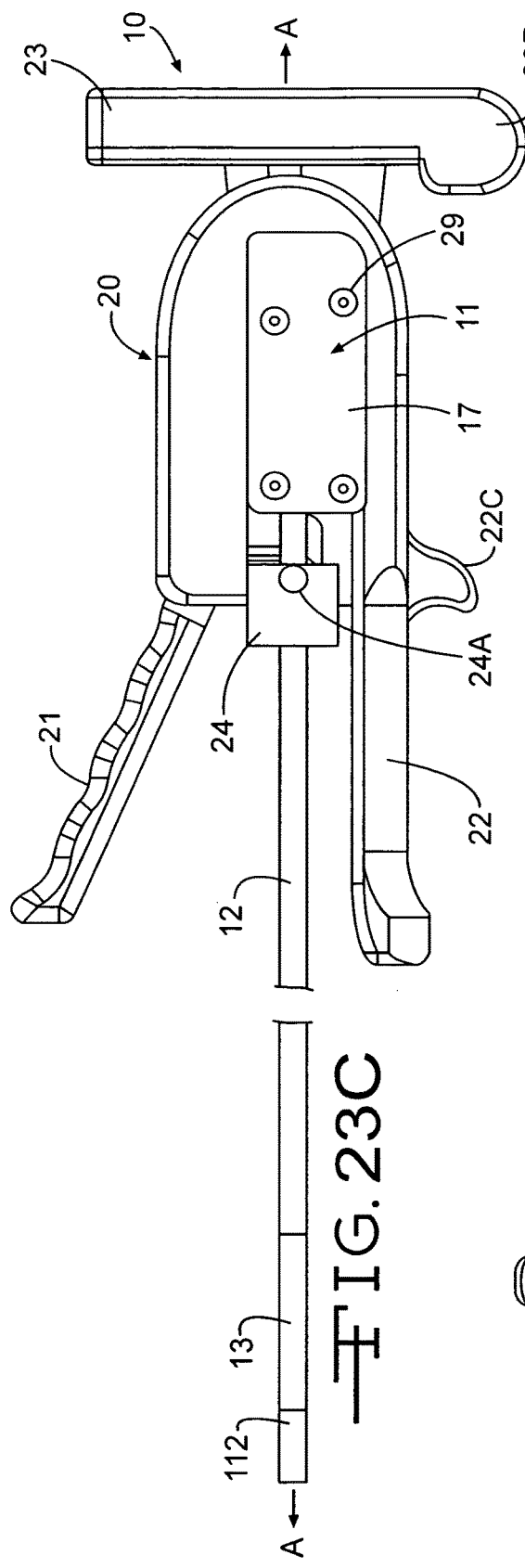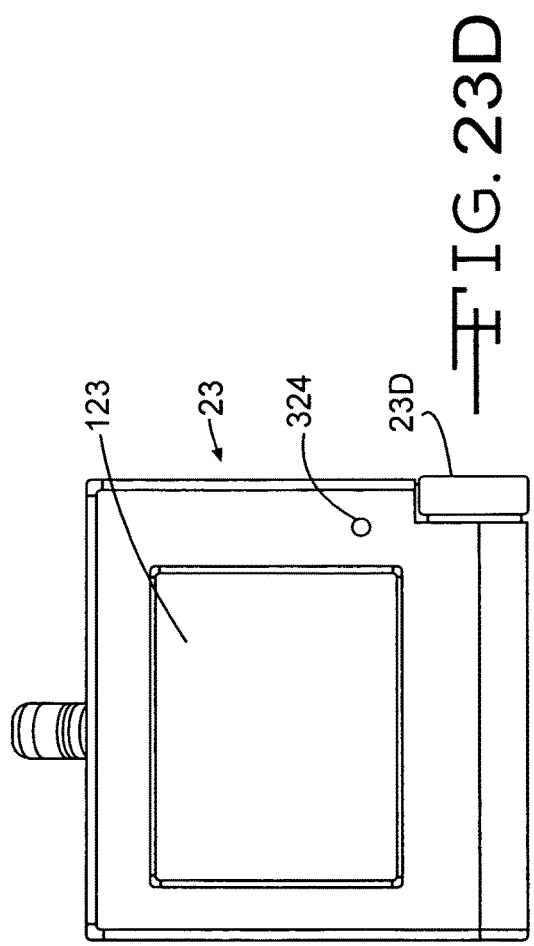

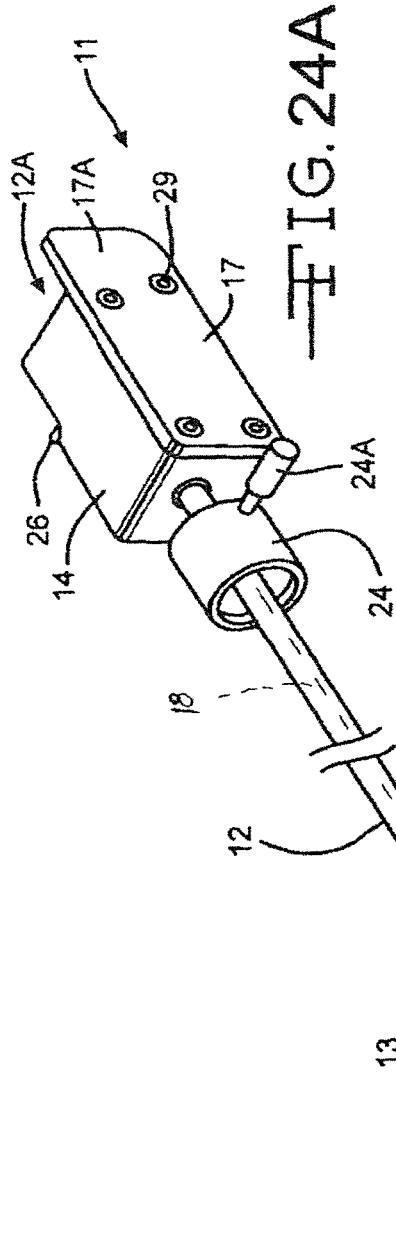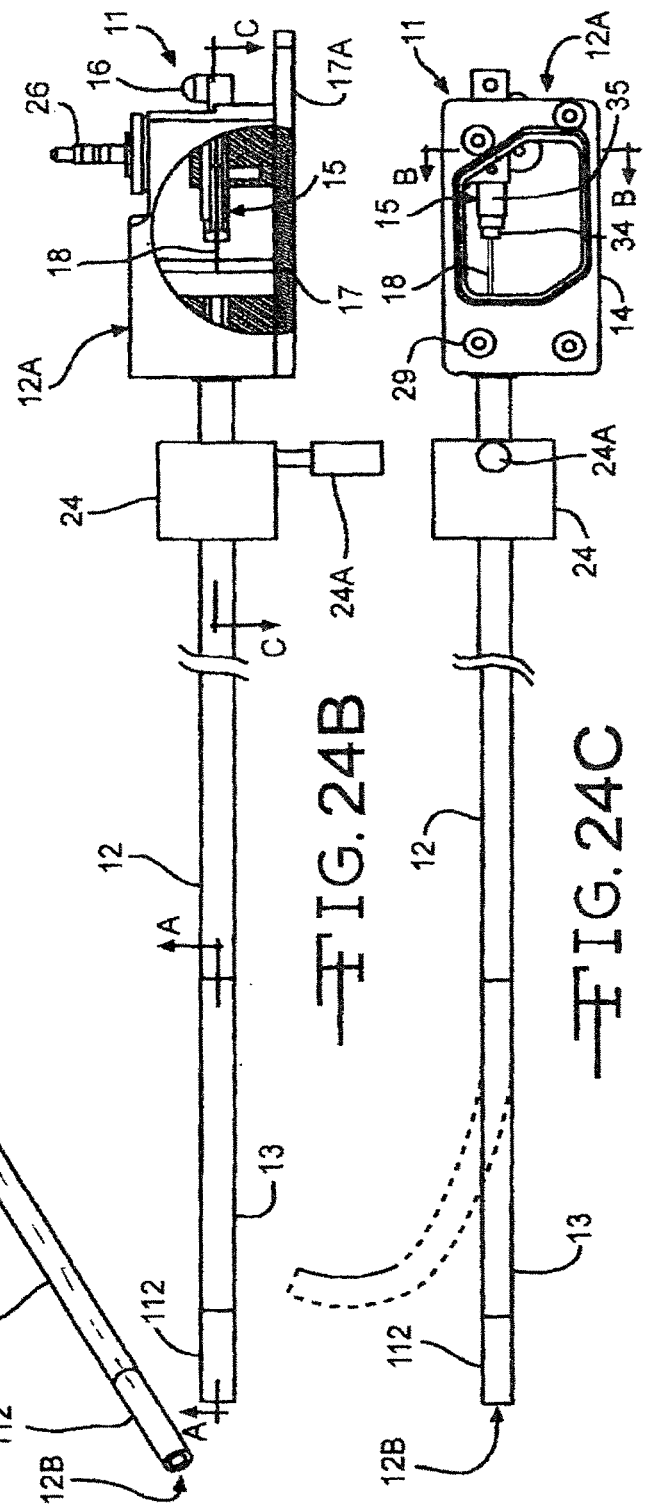

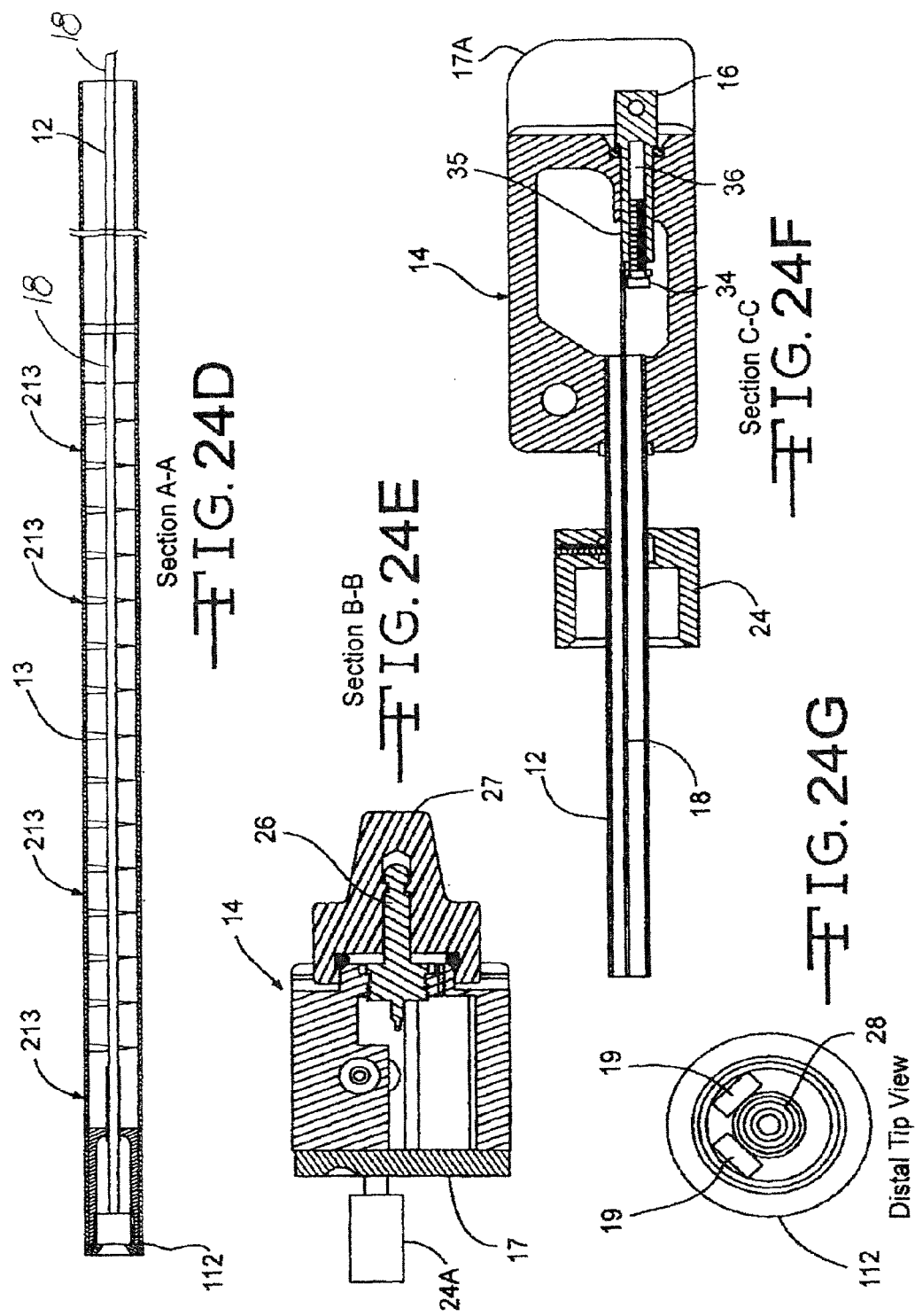

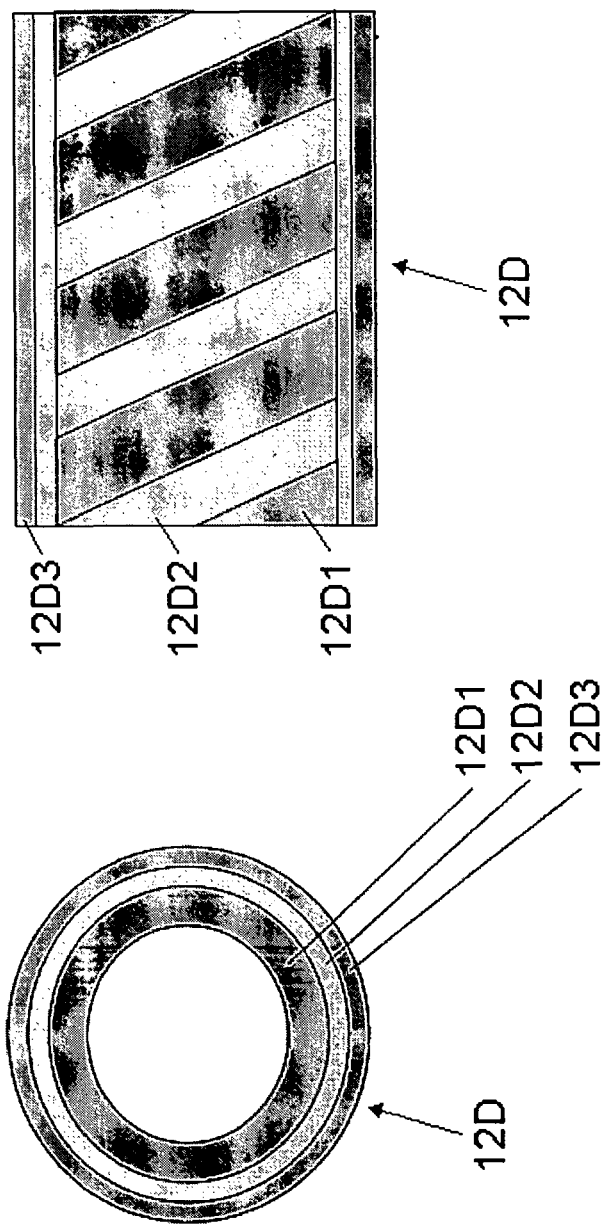

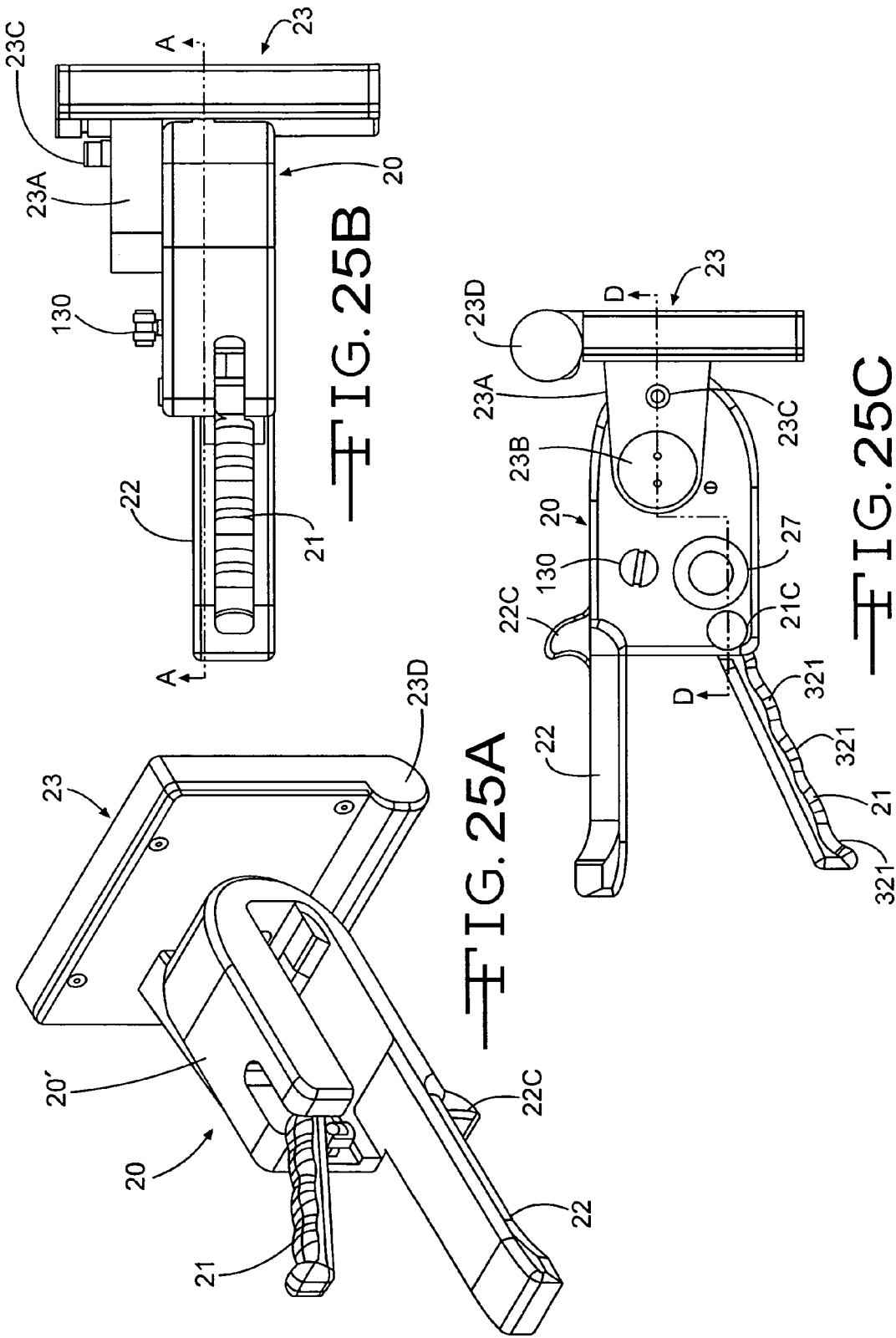

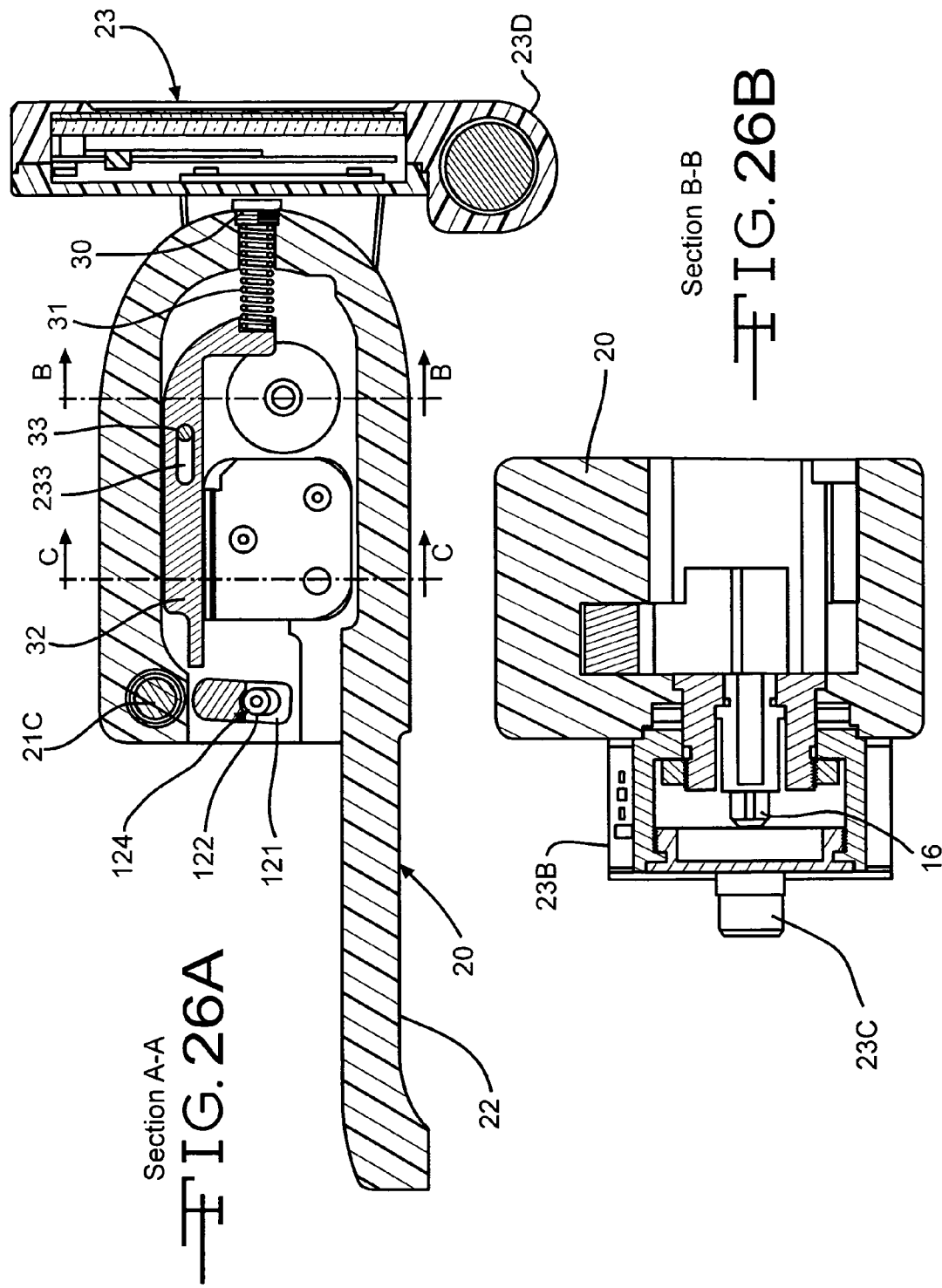

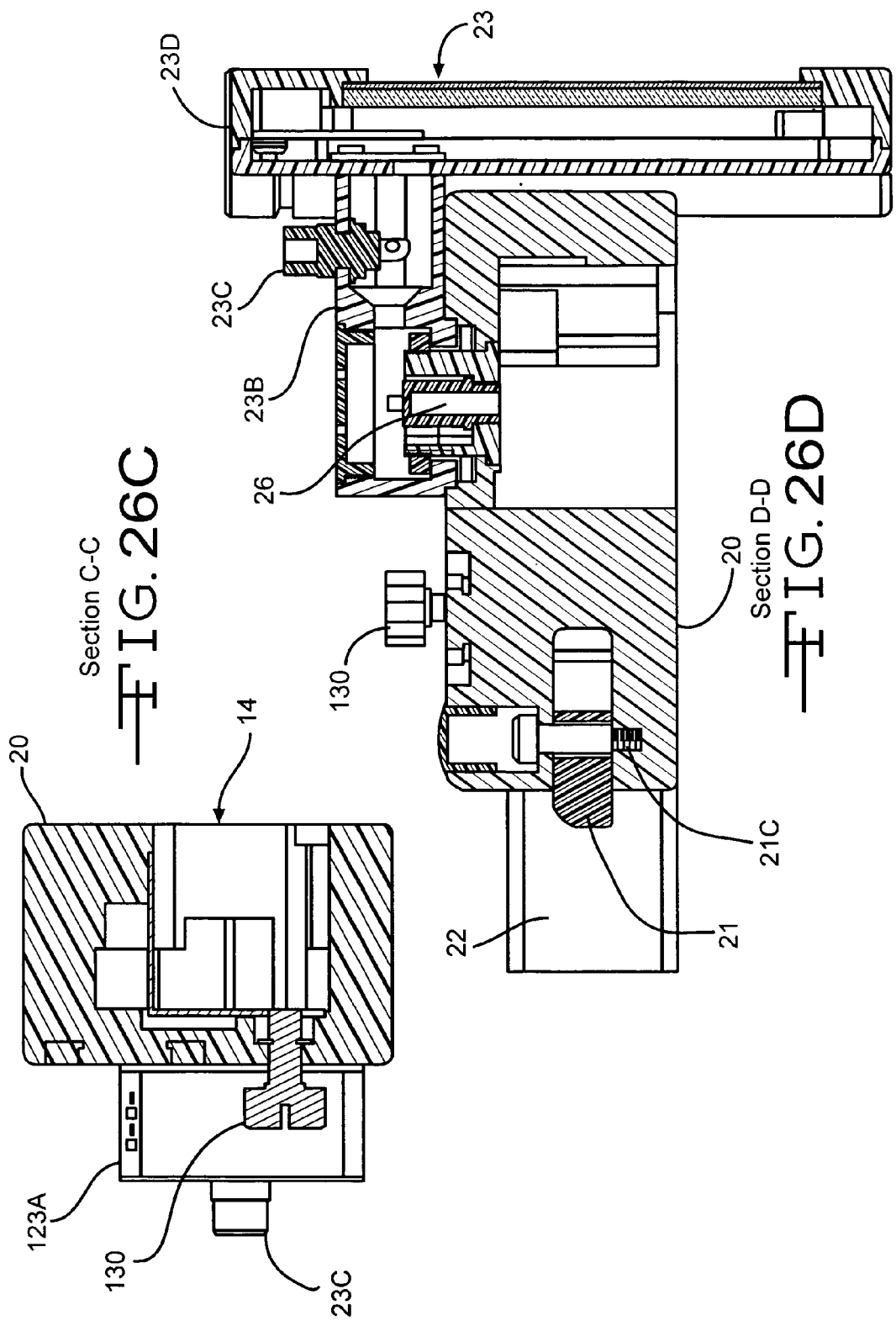

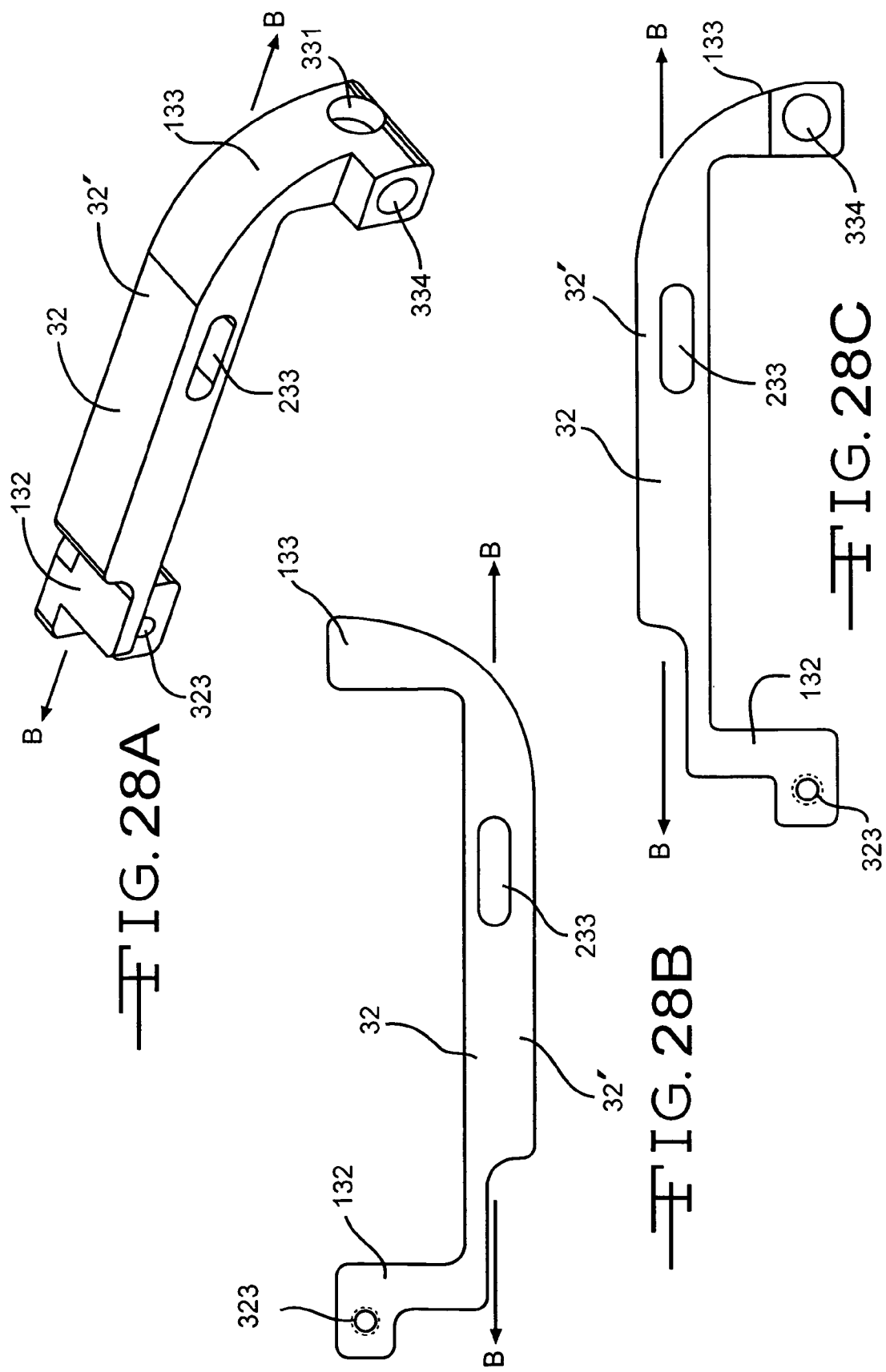

ENDOTRACHEAL INTUBATION DEVICE

BACKGROUND OF THE DISCLOSURE (1) Field of the Disclosure

The present disclosure relates generally to endotracheal intubation devices, and more specifically to endotracheal devices having a detachable stylet, in particular having rigid and flexible portions to facilitate nasal endotracheal intubation, and internal optics or a viewing device coupled to a monitor on an easy to use hand grip.

(2) Description of Related Art

U.S. Pat. No. 2,975,785 to Sheldon discloses an optical viewing instrument comprising an endoscope sheath and a plurality of tube elements arranged in an end to end relationship. One end of the sheath is secured to a control housing and has its interior end in communication with the interior chamber of the housing. The control housing serves to support various control structures for the endoscope including cables which are secured to a terminal tube element with the other ends of the cables secured and looped around a pair of pulleys positioned within the chamber. The pulleys are turned by control knobs to flex a terminal section of the endoscope. The instrument has an optical system with a flexible bundle of optically aligned transparent glass fibers. The transparent glass fibers transmit light from an object which is illuminated by a pair of lamps in the end of the instrument so that an image of the object can be seen at an eyepiece.

U.S. patents issued to Bazinet (U.S. Pat. No. 3,162,214), Takahashi et al. (U.S. Pat. No. 4,236,509) and Petruzzi (U.S. Pat. No. 4,669,172) disclose flexible tubular structures composed of coiled wire and/or tethered circular ring elements which provide for flexibility in tubular structures. Petruzzi discloses a method for fabricating a flexible shaft comprising a spiral cut member having an essentially uniform inside diameter and a tapered linear profile.

U.S. Pat. No. 4,846,153 to Berci discloses an intubating video endoscope which includes an elongated sheath member with a selectively controllable bendable section housing an image forming optical system. A generally rigid section includes a control housing. An image transmitting optical system extends throughout the length of the sheath member and terminates adjacent to the image forming system. A light transmitting system also extends throughout the length of the sheath member to the image forming optical system, the rearward end of which is adapted to be operatively connected to a light source.

U.S. Pat. No. 4,877,016 issued to Kantor et al., discloses a video endoscopic microscope which includes an integral optical element which includes a lens system and an objective lens that is recessed approximately 15 mm from the distal end of the endoscope. An integral illuminating element includes a fiber optic bundle that terminates at the distal end of the endoscope and illuminates the region of the distal end. The lens system terminated in a viewing port that is laterally displaced from the proximal end of the endoscope and which connects to a high resolution video camera that can display a magnified image on a high resolution video monitor, thus obviating the need for an unimpaired visual path from the proximal to the distal end of the endoscope.

U.S. Pat. No. 4,949,716 issued to Chenoweth discloses a hand held medical device with a wide range of nasally placed airway tubes to afford better control of airway tubes. A soft flexible tube surrounding a flat spring has a braided wire which is pulled to control the flexing of the airway tube.

U.S. Pat. No. 6,539,942 to Schwartz et al., hereby incorporated by reference in its entirety, describes an endotracheal intubation device having a series of interlinked, truncated ring-like elements disposed along the distal portion of the tube and a handgrip for controlling the degree of bend in the distal end of the device. An imaging device, such as a nasopharyngoscope, can be inserted through the intubation device to visualize the patient's vocal cords during the intubation procedure. The endotracheal intubation device uses a scissors mechanism without pulleys to bend the distal end of the device.

U.S. Pat. No. 4,905,666 to Fukuda, U.S. Pat. No. 5,520,222 to Chikama and JP 5,329,095 to Ogino teach bending devices which use pulleys or chain driven winding mechanisms which are controlled by cranks and knobs.

U.S. Patent Application 2006/0004258 to Sun et al. discloses an image-type intubation-aiding device comprising a small-size image sensor and a light source module both placed into an endotracheal tube to help doctors with quick intubation. Light from light emission devices in the light source module passes through a transparent housing and is reflected by a target and then focused. The optical signal is converted into a digital or analog electric signal by the image sensor for displaying on a display device after processing. Doctors can thus be helped to quickly find the position of trachea, keep an appropriate distance from a patient for reducing the possibility of infection, and lower the medical treatment cost. Disposable products are available to avoid the problem of infection. The intubation-aiding device can be used as an electronic surgical image examination instrument for penetration into a body. Moreover, a light source with tunable wavelengths can be used to increase the spot ratio of nidus.

U.S. Patent Application 2007/0162095 to Kimmel et al. discloses visualization stylets and methods of use, in which the visualization stylets include modular components that allow interchangeability of imaging devices and lenses, and the use of forward-facing or lateral-facing lens orientations. Optionally, the lens may be focused remotely. A reduced insertion profile is provided by configuring the circuitry of the imaging device so that it is disposed substantially perpendicular to a plane of a pixel array of the imaging device.

U.S. Pat. No. 7,458,375, U.S. Pat. No. 7,658,708, U.S. Publication No. 2008/0200761, and U.S. Publication No. 2008/0308098 to Schwartz et al. are directed to endotracheal intubation devices having a curvable portion and internal optics or a viewing device which facilitate the insertion of an endotracheal tube into a patient.

U.S. Publication No. 2008/0208000 to Schwartz et al. is directed to a device for endotracheal intubation and fluid delivery into the trachea of a patient, The fluid delivery device includes a tubular housing adapted to be sealably mounted on an elongate element of the endoscope and delivers a fluid thereto.

U.S. Publication No. 2009/0090357 to Schwartz et al. is directed to a guide device for facilitating the insertion of a medical device into the trachea of a patient.

While the related art teach endotracheal intubation devices, there still exists a need for an improved endotracheal device having a convenient and effective hand grip, a detachable stylet to allow for easy and convenient disinfection, an effective control wire mechanism, and a stylet that facilitates an endotracheal intubation procedure via the patient's nasal cavity.

OBJECTS

Therefore, it is an object of the present disclosure to provide an improved endotracheal intubation device having a curvable portion controlled by a mechanism that allows for direct griping of the trigger for improved handling.

It is further an object of the present disclosure to provide an endotracheal intubation device having a detachable stylet that is easily connectable with a hand grip.

It is further an object of the present disclosure to provide an endotracheal intubation device having a hand grip with a more pronounced stop and convenient gripping.

It is a further object of the present disclosure to provide an improved stylet assembly for an endotracheal intubation device, where the stylet assembly includes a flexible portion to permit insertion of the stylet assembly (and corresponding endotracheal tube) into a patient's trachea via the nasal cavity.

These and other objects will become increasingly apparent by reference to the following description.

SUMMARY

In an embodiment, the disclosure provides a detachable stylet assembly adapted for endotracheal intubation of a patient, the assembly comprising: (a) an elongated tube as a stylet for the intubation defining: a longitudinal axis, a proximal end for detachably mounting the detachable stylet to a hand grip, and a distal end for entering the trachea of the patient; wherein the elongated tube comprises (i) a rigid section adjacent the proximal end, (ii) an articulation section adjacent the distal end and adapted to curve into the patient's trachea upon actuation, and (iii) a flexible section between the rigid section and the articulation section, the flexible section being adapted to curve to an internal shape of at least one of the patient's nose, nasal cavity, pharynx, and larynx (e.g., any portion thereof and/or any combination thereof; the nose, nasal cavity, and pharynx, and optionally larynx; the nasal part of the pharynx); (b) an actuator housing mounted on and adjacent to the proximal end of the rigid section of the elongated tube, the actuator housing comprising an actuating assembly having connection means for engaging the hand grip; and (c) a control wire mounted within the actuator housing and connected to the actuating assembly, wherein the control wire extends through the elongated tube to the distal end of the elongated tube and is adapted to curve the articulation section upon actuation.

In another embodiment, the disclosure provides an endoscope device adapted for endotracheal intubation of a patient, the device comprising: (a) a stylet assembly comprising: (i) an elongated tube as a stylet for the intubation defining: a longitudinal axis, a proximal end, and a distal end for entering the trachea of the patient; wherein the elongated tube comprises (A) a rigid section adjacent the proximal end, (B) an articulation section adjacent the distal end and adapted to curve into the patient's trachea upon actuation, and (C) a flexible section between the rigid section and the articulation section, the flexible section being adapted to curve to an internal shape of at least one of the patient's nose, nasal cavity, pharynx, and larynx (e.g., any portion thereof and/or any combination thereof; the nose, nasal cavity, and pharynx, and optionally larynx; the nasal part of the pharynx); (ii) an actuator housing mounted (e.g., detachably or fixedly mounted) on and adjacent to the proximal end of the rigid section of the elongated tube, the actuator housing comprising an actuating assembly having connection means for engaging the hand grip; and (iii) a control wire mounted within the actuator housing and connected to the actuating assembly, wherein the control wire extends through the elongated tube to the distal end of the elongated tube and is adapted to curve the articulation section upon actuation; and (b) a hand grip mounted to the actuator housing adjacent the proximal end of the elongated tube.

Various modifications and extensions of the disclosed stylet assembly (whether detachably mounted or fixedly mounted to a hand grip) and related endoscope device are possible. For example, the flexible section can be adapted to curve to an internal shape of the nasal part of the patient's pharynx. The elongated tube can comprise an LED mounted adjacent the distal end of the elongated tube and adapted to illuminate a pathway for the stylet to enter the trachea. A tube stop can be mounted on the tube adjacent the actuator housing comprising an adjustment knob and adapted to allow for mounting of an endotracheal tube over and around the elongated tube. The actuator housing can comprise an electrical connection (e.g., coupled to a camera mounted adjacent the distal end of the elongated tube) mounted on the actuator housing and adapted to be coupled to a mating electrical connection port in the hand grip, and can further comprise a removable soak cap mounted on the actuator housing and adapted to be mounted on and cover the electrical connection port when the stylet is being disinfected in a liquid. The assembly can further comprise a hand grip detachably mounted to the actuator housing adjacent the proximal end of the elongated tube, for example a hand grip comprising: (i) a grip housing; (ii) a trigger as a pivotable lever extending from the housing towards the distal end of the elongated tube and away and nonparallel with respect to the longitudinal axis; and (iii) a stationary handle as a base for squeezing the trigger towards the handle when engaged, the base extending towards the distal end and parallel with the elongated tube. The hand grip can further comprise a display means pivotably mounted on the grip housing and electrically connected to a camera mounted adjacent the distal end of the elongated tube.

In another embodiment, the disclosure provides a method of nasal endotracheal intubation of a patient, the method comprising: (a) providing a stylet assembly or related endoscope device according to any of the various disclosed embodiments including a flexible mid-section in the stylet elongated tube; (b) inserting the distal end of the stylet elongated tube into a patient's larynx through the patient's nose, nasal cavity, pharynx, and larynx, wherein the flexible section of the stylet elongated tube bends to adapt the stylet elongated tube to a curved internal shape of at least one of the patient's nose, nasal cavity, pharynx, and larynx; (c) curving the articulation section of the stylet elongated tube to further advance the distal end of the stylet elongated tube into the patient's trachea and to position an endotracheal tube in the patient's trachea; and optionally (d) removing the stylet elongated tube from the patient through the patient's nose while maintaining the endotracheal tube in place inserted into the patient's trachea. In a refinement of the method, during insertion of the distal end of the stylet in part (b), the flexible section of the stylet elongated tube bends to adapt the stylet elongated tube to a curved internal shape of the nasal part of the patient's pharynx.

The present disclosure provides for a detachable stylet assembly adapted for endotracheal intubation of a patient comprising: (a) an elongated tube as a stylet for the intubation defining: a longitudinal axis, a proximal end for detachably mounting the detachable stylet to a hand grip, and a distal end for entering the trachea of the patient; wherein the tube comprises an articulation section adjacent the distal end adapted to curve into the trachea upon actuation; (b) an actuator housing mounted on and adjacent to the proximal end of the tube comprising an actuating assembly having connection means for engaging the hand grip; and (c) a control wire mounted within the actuator housing and connected to the actuating assembly, wherein the control wire extends through the tube to the distal end of the tube and is adapted to curve the articulation section upon actuation. In an exemplary embodiment, the elongated tube comprises an LED mounted adjacent the distal end of the elongated tube and adapted to illuminate a pathway for the stylet to enter the trachea. In a further embodiment, a tube stop is mounted on the tube adjacent the actuator housing comprising an adjustment knob and adapted to allow for mounting of an endotracheal tube over and around the elongated tube. Typically, the hand grip is detachably mounted to the actuator housing adjacent the proximal end of the elongated tube. In an even further embodiment, the actuator housing comprises an electrical connection mounted on the actuator housing and adapted to be coupled to a mating electrical connection port in the hand grip. The assembly typically comprises a removable soak cap mounted on the hand grip and adapted to be mounted on and cover the electrical connection port when the stylet is being disinfected in a liquid. The soak cap can be colored a distinguishing color to be identifiable from the other components of the hand grip. The electrical connection port can be coupled to a camera mounted adjacent the distal end of the elongated tube.

The hand grip generally comprises: (i) a grip housing; (ii) a trigger as a pivotable lever extending from the housing towards the distal end of the elongated tube and away and nonparallel with respect to the longitudinal axis; and (iii) a stationary handle as base for squeezing the trigger towards the handle when engaged, the base extending towards the distal end and parallel with the elongated tube. The lever engages the actuating assembly through the connection means and is adapted to cause the control wire to curve when the trigger is squeezed. In an exemplary embodiment, the connection means is a stem protruding outside the actuator housing and connecting to a hole defined on an actuator linkage mounted in the grip housing which is engaged with the trigger. The stem typically extends perpendicular with respect to the longitudinal axis out of the actuator housing. In a further embodiment, the hand grip comprises a display means pivotably mounted on the grip housing and electrically connected to the camera through the electrical connection. The display means can be a LCD screen. In an even further embodiment, the stationary handle further comprises a stop substantially curved perpendicular to the base to provide a physical stop to a user when gripping the hand grip. The trigger can comprise finger grooves for convenient gripping.

The present disclosure further provides for a hand grip adapted for endotracheal intubation with a detachable stylet comprising: (a) a grip housing defining a longitudinal axis extending from the grip housing; (b) a base handle essentially parallel with the longitudinal axis of the grip housing; and (c) a lever as a trigger mounted in and extending from the grip housing, the lever extending away from the base handle and nonparallel with respect to the longitudinal axis. The grip housing is configured to allow for mounting of an actuator means for moving a control wire in an elongated tube as a stylet extending along the longitudinal axis. The trigger is adapted to control movement of the control wire through a connection in the actuator means when the trigger is squeezed. In an exemplary embodiment, the stationary handle further comprises a stop substantially curved perpendicular to the base to provide a physical stop to a user when gripping the hand grip. In a further embodiment, the trigger comprises finger grooves for convenient gripping. The grip housing typically provides means for mounting a display monitor. The means for mounting a display monitor can be a pivotable mounting member adapted to allow for pivoting of the display monitor of 180 degrees about a plane defined by the grip housing. The display monitor can be mounted on a swivel adapted to allow for radial movement of the display about the swivel. In an even further embodiment, the hand grip comprises an electrical connection port coupled to a mating electrical port on the actuator means adapted to provide electrical connection between the display monitor and a camera mounted adjacent a distal end of the elongated tube. The grip housing can further comprise a video out port for optional external viewing. The actuator means can be a detachable stylet adapted to be detachably mounted within the handgrip.

The present disclosure further provides for an endoscope device comprising: (a) an elongated tube as a stylet defining a longitudinal axis mounted on an actuator housing and having a curvable portion at a distal end of the elongated tube comprised of: (i) a connecter member mounted in the housing; and (ii) a control wire attached to a proximal end that extends through the elongated tube along the longitudinal axis to the distal end of the elongated tube; and (b) a hand grip comprising: (i) a grip housing; (ii) a base handle extending from the grip housing parallel with the longitudinal axis of the elongated tube; (iii) a lever as a trigger extending from the grip housing and away and nonparallel with respect to the base handle; (iv) an actuator linkage defining a connector end connected to the connector member and a lever end connected to the trigger, wherein the actuator linkage is mounted in the grip housing and is adapted to translate linearly parallel to the longitudinal axis when the trigger is squeezed towards the base handle; and (v) a tension spring abutting against the actuator linkage for returning the actuator linkage to rest once the trigger is no longer being squeezed. The trigger is adapted to be squeezed causing the trigger to pivot towards the base handle. The squeezing of the trigger translates the actuator linkage linearly away from the elongated tube which causes the connector member and the control wire to translate linearly away from the elongated tube and curve the curvable portion at the distal end of the elongated tube. The actuator housing can be detachable from the hand grip. In an exemplary embodiment, the device further comprises a display monitor pivotably mounted on a pivot member mounted on the grip housing. The display monitor can be electrically connected through the grip housing and the actuator housing to a camera mounted adjacent the distal end of the elongated tube. The actuator housing typically comprises an electrical connector coupled to the camera at the distal end of the elongated member and the grip housing comprising a mating electrical port within the grip housing and connected to the display monitor. The mounting of the actuator housing to the hand grip connects the electrical connector of the actuator housing to the mating electrical port of the grip housing. In a particularly embodiment, the actuator linkage slides linearly along a pair of spaced apart guide posts mounted in the grip housing and positioned in parallel with the longitudinal axis. In a further embodiment, the actuator linkage slides linearly along a guide post mounted in the grip housing and positioned in parallel with the longitudinal axis. In an even further embodiment, the connector member is a stem protruding outside the actuator housing and connecting to a hole defined on an actuator linkage mounted in the grip housing which is engaged with the trigger. The stem generally extends perpendicular with respect to the longitudinal axis out of the actuator housing. In yet a further embodiment, the stationary handle further comprises a stop substantially curved perpendicular to the base to provide a physical stop to a user when gripping the hand grip. In yet an even further embodiment, the trigger comprises finger grooves for convenient gripping. The elongated tube can further comprise a plunger connected to the connector member adapted to translate within a chamber along the longitudinal axis and wherein the control wire is attached to the plunger at the proximal end. The plunger typically translates linearly away from the elongated tube causing the control wire to translate linearly and curve the curvable portion at the distal end of the elongated tube when the trigger is squeezed.

The present disclosure further provides for a method of endotracheal intubation of a patient comprising the steps of: (a) providing a detachable stylet assembly mounted to a hand grip adapted for endotracheal intubation of a patient comprising: (i) an elongated tube as a stylet for the intubation defining: a longitudinal axis, a proximal end for detachably mounting the detachable stylet to a hand grip, and a distal end for entering the trachea of the patient; wherein the tube comprises an articulation section adjacent the distal end adapted to curve into the trachea upon actuation; (ii) an actuator housing mounted on and adjacent to the proximal end of the tube comprising an actuating assembly having connection means for engaging the hand grip; (iii) a control wire mounted within the actuator housing and connected to the actuating assembly, wherein the control wire extends through the tube to the distal end of the tube and is adapted to curve the articulation section upon actuation; (b) inserting the stylet into the trachea of the patient; and (c) curving the articulation section to position a tube into the trachea of the patient.

The present disclosure further still provides for a method of endotracheal intubation of a patient comprising the steps of: (a) providing a hand grip mounted to an actuator means comprising: (i) a grip housing defining a longitudinal axis extending from the grip housing; (ii) a base handle essentially parallel with the longitudinal axis of the grip housing; (iii) a lever as a trigger mounted in and extending from the grip housing, the lever extending away from the base handle and nonparallel with respect to the longitudinal axis; wherein the grip housing is configured to allow for mounting of an actuator means for moving a control wire in an elongated tube as a stylet extending along the longitudinal axis; and wherein the trigger is adapted to control movement of the control wire through a connection in the actuator means when the trigger is squeezed; (b) inserting the stylet into the trachea of the patient; and (c) curving the control wire with the trigger to position a tube into the trachea of the patient.

The present disclosure even further still provides for a method of endotracheal intubation of a patient comprising the steps of: (a) providing an endoscope device comprising: (1) an elongated tube as a stylet defining a longitudinal axis mounted on an actuator housing and having a curvable portion at a distal end of the elongated tube comprised of a connecter member mounted in the housing and a control wire attached to a proximal end that extends through the elongated tube along the longitudinal axis to the distal end of the elongated tube; (2) a hand grip comprising: (i) a grip housing; (ii) a base handle extending from the grip housing parallel with the longitudinal axis of the elongated tube; (iii) a lever as a trigger extending from the grip housing and away and nonparallel with respect to the base handle; (iv) an actuator linkage defining a connector end connected to the connector member and a lever end connected to the trigger, wherein the actuator linkage is mounted in the grip housing and is adapted to translate linearly parallel to the longitudinal axis when the trigger is squeezed towards the base handle; and (v) a tension spring abutting against the actuator linkage for returning the actuator linkage to rest once the trigger is no longer being squeezed; wherein the trigger is adapted to be squeezed causing the trigger to pivot towards the base handle; and wherein the squeezing of the trigger translates the actuator linkage linearly away from the elongated tube which causes the connector member and the control wire to translate linearly away from the elongated tube and curve the curvable portion at the distal end of the elongated tube; (b) inserting the stylet into the trachea of the patient; (c) curving the articulation section with the trigger to position a tube into the trachea of the patient.

BRIEF DESCRIPTION OF THE DRAWINGS

FIG. 2 illustrates a side view of the device of FIG. 1.

FIG. 2A illustrates a side view of the device of FIG. 1A.

FIGS. 3A-3B illustrate an exemplary detachable stylet for the device of FIG. 2.

FIGS. 3C-3D illustrate an exemplary detachable stylet for the device of FIG. 2A.

FIG. 4A-4E illustrate various side views of the device from FIG. 1 showing the display means in different orientations and an exemplary camera mounted in the tip.

FIG. 22 illustrates the device of FIG. 21 with the display means in a rotated, adjusted and swiveled orientation.

FIGS. 23A-23D illustrate an exemplary endotracheal intubation device having an exemplary hand grip with a grooved trigger and a display monitor.

FIG. 24A illustrates a perspective view of an exemplary detachable stylet.

FIG. 24B illustrates a side view of the stylet of FIG. 24A showing the internal components of the actuator assembly.

FIG. 24C illustrates a further side view of the stylet from FIG. 24A rotated 90° from the view of FIG. 24B.

FIG. 24D is a cross section view A-A from FIG. 24B showing an exemplary articulation section.

FIG. 24E is a cross section view B-B from FIG. 24C showing an exemplary soak cap mounted on the electrical connection.

FIG. 24F is a cross section view C-C from FIG. 24B showing an actuating mechanism inside the actuator housing.

FIG. 24G illustrates a distal tip view of the stylet of FIG. 24A.

FIGS. 24H-24I illustrate cross section views of the flexible portion of the style of FIGS. 2A, 3C, and 3D.

FIG. 25A illustrates a perspective view of an exemplary grip housing with a monitor and trigger.

FIG. 25B illustrates a trigger side view of the grip housing of FIG. 25A.

FIG. 25C illustrates a side view showing the mounting and pivoting of the monitor to the grip housing of FIG. 25A.

FIG. 26A is a cross section view A-A of FIG. 25B.

FIG. 26B is a cross section view B-B of FIG. 26A.

FIG. 26C is a cross section view C-C of FIG. 26A.

FIG. 26D is a cross section view D-D of FIG. 25C.

FIG. 28A-28C illustrate an exemplary linkage with a single opening shown in perspective (A) view, backbone side down (B) view, and backbone side up (C) view.

DESCRIPTION OF PREFERRED EMBODIMENTS

All patents, patent applications, government publications, government regulations, and literature references cited in this specification are hereby incorporated herein by reference in their entirety. In case of conflict, the present description, including definitions, will control. The following applications are incorporated by reference herein in their entirety for all purposes: Ser. No. 11/230,392 filed Sep. 20, 2005 (now U.S. Pat. No. 7,658,708), Ser. No. 11/514,486 filed Sep. 1, 2006 (now U.S. Pat. No. 7,458,375), Ser. No. 11/820,117 filed Jun. 18, 2007 (now U.S. Publication 2008/0308098), Ser. No. 11/906,870 filed Oct. 4, 2007 (now U.S. Publication 2009/0090357), Ser. No. 12/148,033 filed Apr. 16, 2008 (now U.S. Publication 2008/0208000), Ser. No. 12/148,050 filed Apr. 16, 2008 (now U.S. Publication 2008/0200761), and Ser. No. 12/587,905 filed Oct. 15, 2009 (now U.S. Publication 2010/0095969).

Figure 1:
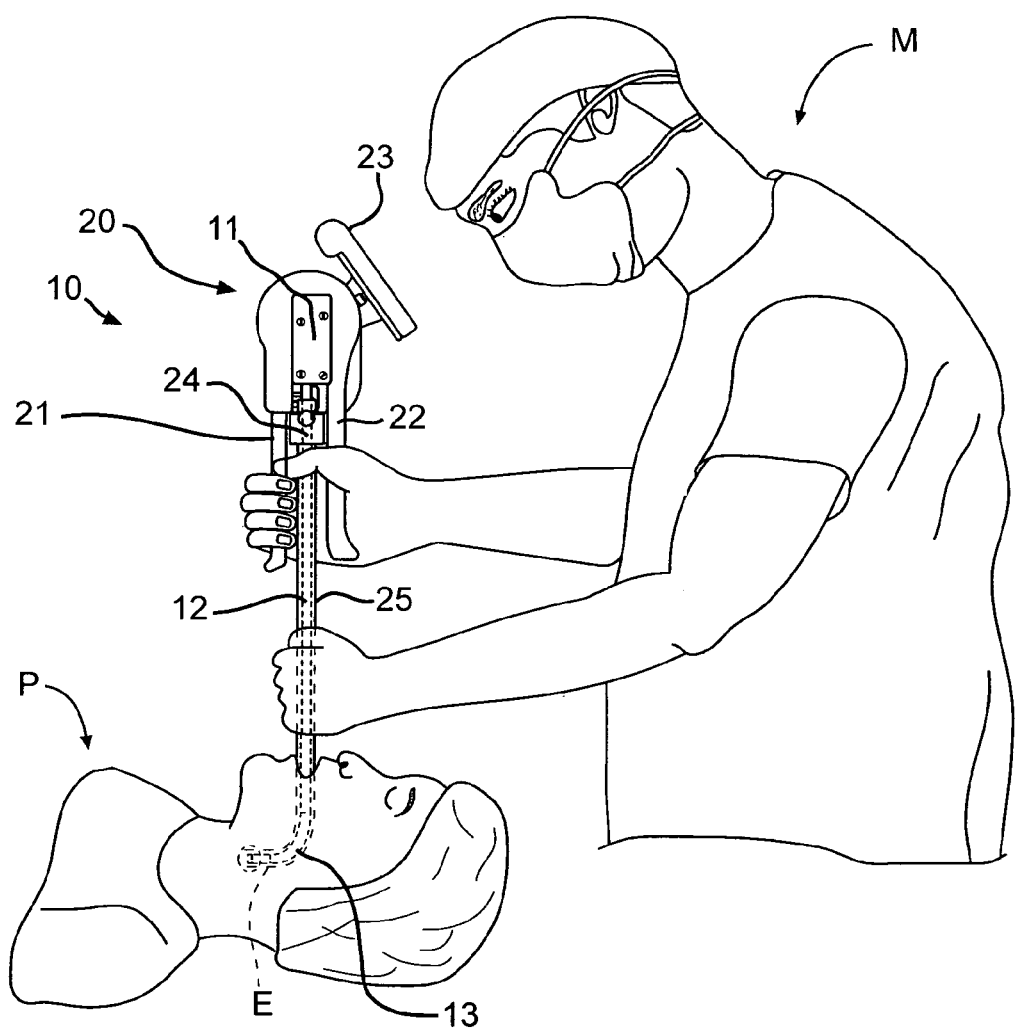
FIG. 1 illustrates an exemplary endotracheal intubation device with a trigger and hand grip in use on a patient by a medical professional.

Referring to FIGS. 1-7, an exemplary endotracheal intubation device is shown having a hand grip 20 with a trigger 21 for convenient articulation of an articulation section 13. FIG. 1 illustrates endotracheal intubation device 10 in use on a patient P. Device 10 is being operated by a medical professional M to access patient P's trachea E. In an exemplary embodiment, device 10 includes a detachable stylet assembly 11 which comprises an elongated tube 12. Stylet assembly 11 is adapted to connect with a hand grip 20. In FIG. 2, elongated tube 12 defines: a longitudinal axis A-A, a proximal end 12A for detachably mounting the stylet to hand grip 20, and a distal end 12B for entering the trachea E of patient P. Tube 12 comprises an articulation section 13 adjacent distal end 12B. Section 13 is adapted to curve into trachea E upon actuation of trigger 21 from hand grip 20. As shown in FIG. 1, articulation section 13 is curved into trachea E of the patient since it is being actuated by the trigger 21 on hand grip 20. The hand grip 20 comprises a trigger 21 that is squeezed by professional M to actuate section 13. Mounted on tube 12 is a tube stop 24 comprising an adjustment knob 24A and adapted to allow for mounting of an endotracheal tube 25 over and around the elongated tube 12. In a particular embodiment, device 10 is used to insert and place endotracheal tube 25 into the patient P to clear the trachea E and then device 10 is subsequently removed leaving endotracheal tube 25 in place for further procedures to be performed.

Detachable stylet assembly 11, as shown detached from hand grip 20 and alone in FIGS. 3A and 3B, comprises an actuator housing 14. Housing 14 defines a substantially rectangular cross section and encloses an actuating assembly 15, as shown in the various magnified and exploded views of FIGS. 9-17 discussed in greater detail below. Actuator housing 14 is mounted on and adjacent to proximal end 12A of tube 12. Actuating assembly 15 comprises a connection means 16 for engaging hand grip 20. Connection means 16 extends out from the enclosure of housing 14 on an opposite side from where tube 12 extends out of housing 14. Connection means 16 can be a stem that is operable to engage trigger mechanism 21 of hand grip 20. This engagement occurs when stylet assembly 11 is connected with hand grip 20. Actuator housing 14 includes a back plate 17 for protecting internal components of actuator assembly 15 from the external environment. Back plate 17 includes an extension 17A that lays flush with hand grip 20 when stylet 11 is attached. This provides external protection for connection means 16.

Medical professional M typically stands at the head of patient P when intubating. As tube 12 is inserted into the trachea E of patient P, medical professional P can squeeze trigger 21 which is connected through connection means 16 to actuator assembly 15. Actuator assembly 15 connects to a control wire 18 (shown in FIGS. 9, 10, 12, 13, and 17). Control wire 18 is mounted within actuator housing 14 and connected to the connection means 16. Control wire 18 extends through tube 12 to distal end 12B and is adapted to curve the articulation section 13 upon actuation. Actuation occurs when trigger 21 is squeezed. In an exemplary embodiment, articulation section 13 is curvable via a vertebrae configuration or a Nitinol tube as described with respect to U.S. patent application Ser. No. 12/148,050 filed Apr. 16, 2008. While the elongated tube 12 can be constructed of stainless steel, polymer or other sturdy material, in some preferred embodiments it is constructed of a shape memory alloy (SMA). Any shape memory alloy such as a copper-zinc-aluminum, copper-aluminum-nickel, and nickel-titanium (NiTi) alloys can be used, such as, but not limited to Nitinol. The articulation or curvable portion 13 of elongated tube 12 can be constructed of a shape memory alloy such as Nitinol. The shape memory alloy (SMA) of the articulation section 13 will flex when the trigger 21 is squeezed, and then will return to its original conformation when the trigger 21 is released due to the tendency of the SMA to spring back to a less curved conformation.

FIGS. 2A, 3C, and 3D illustrate an additional embodiment of a stylet assembly 11A that includes a flexible portion to facilitate the endotracheal intubation of a patient through the patient's nose (i.e., instead of the patient's mouth). Similar to FIGS. 2, 3A, and 3B, the stylet assembly 11A includes an elongated tube 12 with a proximal end 12A (e.g., mounted to the actuator housing 14) and a distal end 12B. Relative to the previous embodiment, the elongated tube 12 includes (i) a rigid section 12C adjacent the proximal end 12A (e.g., extending to the housing 14 and being mounted thereto), (ii) an articulation section 13 adjacent the distal end 12B (e.g., extending to the distal end 12B of the tube 12), and (iii) a flexible section 12D between the rigid section 12C and the articulation section 13. The rigid section 12C, flexible section 12D, and the articulating section 13 may be directly or indirectly mounted or connected to each other (e.g., with or without any intervening tubular or other structure permitting passage of the control wire 18 therethrough) and together define a passage for the control wire 18 to extend between the housing 14/proximal end 12A of the tube 12 and the distal end 12B of the tube 12. The rigid section 12C can be formed from any rigid material that generally maintains its shape and remains aligned with the longitudinal axis A-A defined by the elongated tube 12 in its substantially straight, extended configuration shown in FIG. 2A. Suitable rigid materials include metals (e.g., stainless steel, copper, brass) and polymers (e.g., sturdy/rigid thermoplastic or thermoset materials), for example those having a generally tubular shape. The articulating section 13 is the same as described herein and illustrated in the various figures. Actuation of the control wire 18 generally causes the articulating section 13 to curve, for example in the +θ-direction and within the plane defined by the θ-direction and the longitudinal axis A-A (e.g., as illustrated in FIG. 2A (showing the direction and plane) and in FIG. 4B (showing the curved articulating section 13).

The structure of the flexible section 12D is not particularly limited and can be formed from any flexible material (e.g., material that is itself flexible or a composite structure of rigid components that are together flexible) that permits independent movement of the flexible section 12D relative to the rigid section 12C and the articulation section 13. The control wire 18 is suitably aligned substantially at or near the center/axis defined by the cross section of the flexible section 12D to that a tension applied to the control wire 18 will curve the articulating section 13 as desired but preferably will not induce a substantial bending moment to the flexible section 12D. Preferably, the flexible section 12D is capable of bending in any direction, for example positive and/or negative deflection in either or both of two mutually orthogonal directions also orthogonal to the longitudinal axis A-A (e.g., +θ-direction, −θ-direction, +φ-direction, and/or −φ-direction relative to the axis A-A shown in FIGS. 2A and 3B). The flexible section 12C can be bent manually by the medical professional M and/or can bend naturally as it conforms the shape of a patient's internal passageways during an intubation procedure/insertion. While the flexible section 12D is deformable relative to the axis A-A as described above, the section 12D suitably has sufficient torsional strength so that a rotation applied to the elongated tube 12 causes the components of the elongated tube 12 to rotate as a solid body (e.g., a twisting force/rotational movement applied medical professional M via the hand grip 20 around the axis A-A results in substantially the same relative rotational movement of the distal end 12B and articulating section 13 of the tube 12).

FIGS. 24H and 24I illustrate axial and lateral cross sections of a suitable structure for the flexible section 12D. As shown, from outside to inside, the flexible section 12D has a layered construction including a flexible plastic jacket 12D3 (e.g., a polyurethane), a braided tube 12D2, and a spiral-wrapped flat wire 12D1. The jacket 12D3 seals the section 12D from the external environment (e.g., and the jacket 12D3 optionally can extend as an outer covering over the rigid section 12C and/or articulating section 13), the braided tube 12D2 provides torsional strength, and the spiral-wrapped flat wire 12D1 provides crush resistance. Other suitable configurations (not shown) for the flexible section 12D can include a flexible plastic tube (e.g., a flexible polymer having a tube wall suitably thick to provide torsional strength and crush resistance), a shape memory material, and a flexible composite structure formed from rigid components (e.g., a rigid metal or plastic material having a ball-and-socket composite structure or a vertebrae composite structure, such as that illustrated in FIG. 24D, but capable of moving in multiple directions).

The stylet assembly 11A is otherwise analogous to the stylet assembly 11, with like numerals representing analogous structural elements. Similarly, the stylet assembly 11A is interchangeable with the stylet assembly 11 in terms of its ability to interact/interface with other endoscope components described herein (e.g., the hand grip 20).

Figure 1A:
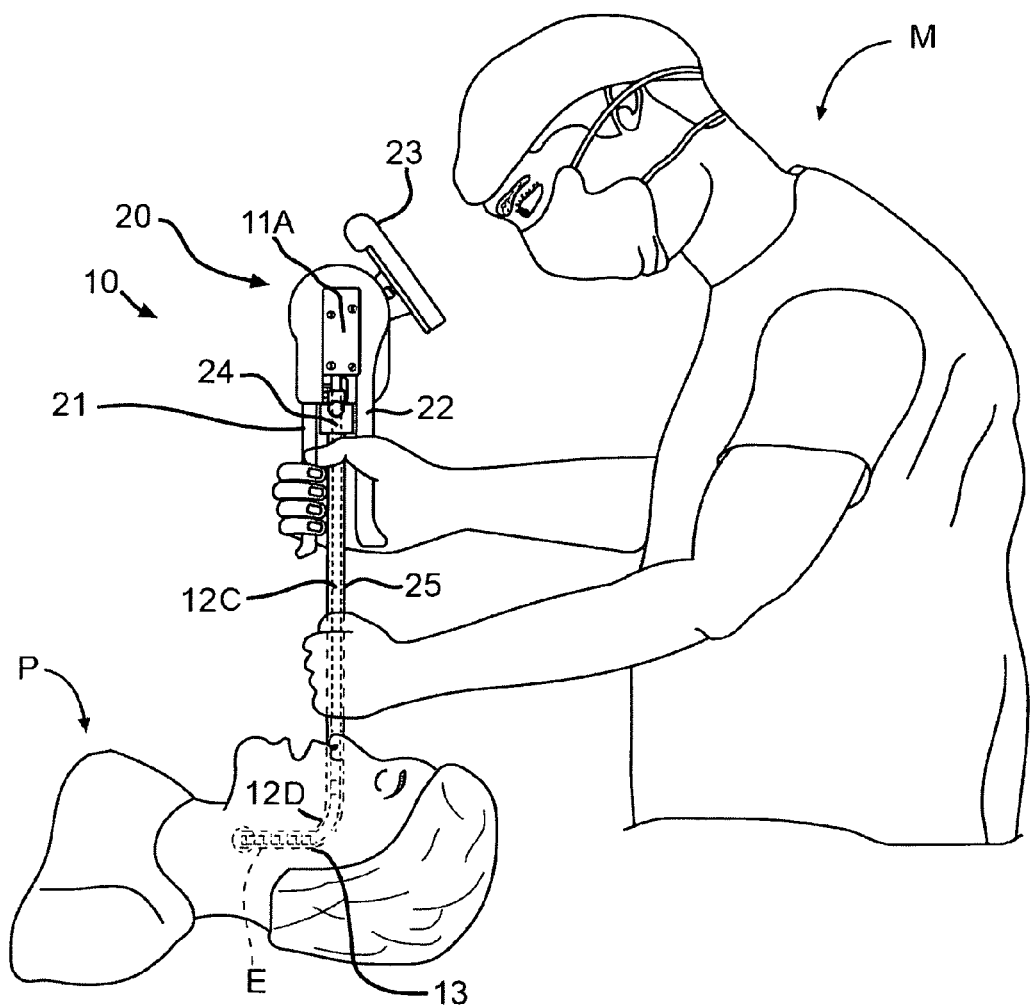
FIG. 1A illustrates an exemplary endotracheal intubation device with a trigger, hand grip, and a flexible, articulatable stylet in use on a patient by a medical professional for a nasal endotracheal intubation procedure.

FIG. 1A illustrates a nasal endotracheal intubation method for a patient P similar to that shown in FIG. 1. In this case, the distal end 12B of the tube 12 and stylet assembly 11A (e.g., also including an endotracheal tube 25 mounted around or adjacent the tube 12) is inserted into the patient P through (in succession) the patient's nose, nasal cavity, pharynx (e.g., including, also in succession, the nasal, oral, and laryngeal parts thereof), and larynx so that the distal end 12B of the tube 12 is adjacent/near the patient's trachea E. The freely flexible nature of the flexible section 12D facilitates nasal intubation by permitting the flexible section 12D to bend, adapt, and otherwise conform to the various curves of the internal nasal, pharyngeal, and laryngeal passageways in the patient P as the tube 12 is being inserted (i.e., the flexible section 12D naturally bends in response to the gradual insertion of the tube 12 by the medical professional M and the interaction between the flexible section 12D and the walls of the patient's internal passageways). A notable point of internal curvature accommodated by the flexible section 12D is the curved transition between the nasal cavity and pharynx, for example the nasal part of the pharynx between the nasal cavity and the oral part of the pharynx. If desired, at least partial actuation/curving of the articulating section 13, twisting/rotation of the handgrip 20, and/or visualization using a camera mounted in the tube 12 can be used to further assist navigation and insertion of the tube 12 via the nasal route.

In the illustrative embodiment shown in FIG. 1A, the tube 12 has been inserted through the nose to a point such that the distal end 12B of the tube 12 and the articulating section 13 is adjacent/near the patient's trachea E, ready for further insertion therein. In this case, a portion of the flexible section 12D is substantially straight (e.g., a proximal portion in the nose and nasal cavity as shown), and a portion of the flexible section 12D is bent and adapted to the curved internal shape of the patient's internal passageways (e.g., a distal portion of the section 12D generally at the curved transition between the nasal cavity and pharynx, for example the nasal part of the pharynx). As the tube 12 is further inserted to the trachea E to complete the endotracheal intubation process (e.g., by curving the articulation section 13 of the tube 12 and advancing the distal end 12B thereof into the trachea E), the flexible section 12D further bends to accommodate the patient's internal passageways. For example, a distal portion of the flexible section 12D will become substantially straight or slightly curved to accommodate the internal space between (i) the oral part of the pharynx and (ii) the laryngeal part of the pharynx and/or the larynx. Similarly, a proximal portion of the flexible section 12D (e.g., which was previously in the nasal cavity) will bend to accommodate the curved nasal part of the pharynx, and a distal portion of the rigid section 12C may enter the nasal cavity (e.g., depending on the length of the flexible section 12D relative to the patient's internal passageways). Because the flexible section 12D naturally conforms to the patient's internal passageways, the size of the flexible section 12D (e.g., its length and/or diameter) should be suitably scaled according to the size of the patient and the corresponding internal passageways for nasal intubation as compared to oral intubation.

The stylet assembly 11A, in addition to the described nasal endotracheal intubation method, also generally can be used in an oral endotracheal intubation method as disclosed herein (e.g., as illustrated in FIG. 1 and described with respect to the stylet assembly 11). In this case, the flexible section 12D is adapted to curve to an internal shape of one or more of the patient's mouth, pharynx (e.g., oral part thereof, laryngeal part thereof), and larynx (e.g., also including any portion thereof or any combination thereof), and the flexible section 12D bends accordingly as the distal end 12B of the stylet elongated tube 12 is inserted therethrough during the intubation process. In an embodiment, the stylet elongated tube 12 can be inserted into a patient through a (generally tubular) medical device that has been previously placed/inserted into one or more of a patient's nasal cavity, mouth, pharynx (including any portions thereof), and larynx. In this case, the flexible section 12D facilitates insertion of the stylet elongated tube 12 of the pre-existing medical device insofar as the flexible section 12D bends to adapt to the curvature of the pre-existing medical device (e.g., which also can correspond to the general curvature of the patient's internal passageways containing the pre-existing medical device). Suitably, the elongated tube 12 of the stylet assembly 11A can be inserted into a patient (e.g., along with an intubation tube in order to intubate the patient) via a pre-existing, orally placed supraglottic device that is present in the patient's mouth and pharynx (e.g., oral and/or laryngeal parts thereof), in which case the flexible section 12D readily adapts to the curvature of the supraglottic device (e.g., around the patient's tongue and/or at the curved transition from the mouth to the oral part of the pharynx).

In an exemplary embodiment, elongated tube 12 comprises at least one LED light 19 mounted adjacent the distal end 12B of elongated tube 12 as shown in FIG. 4E. LED light 19 is adapted to illuminate a pathway for stylet 10 to enter the trachea E. FIG. 2 illustrates a side view of device 10 with trigger 21 at rest and thus articulation section 13 in a substantially straight configuration. LED light 19 is typically mounted in the tip 112.

Figure 6:
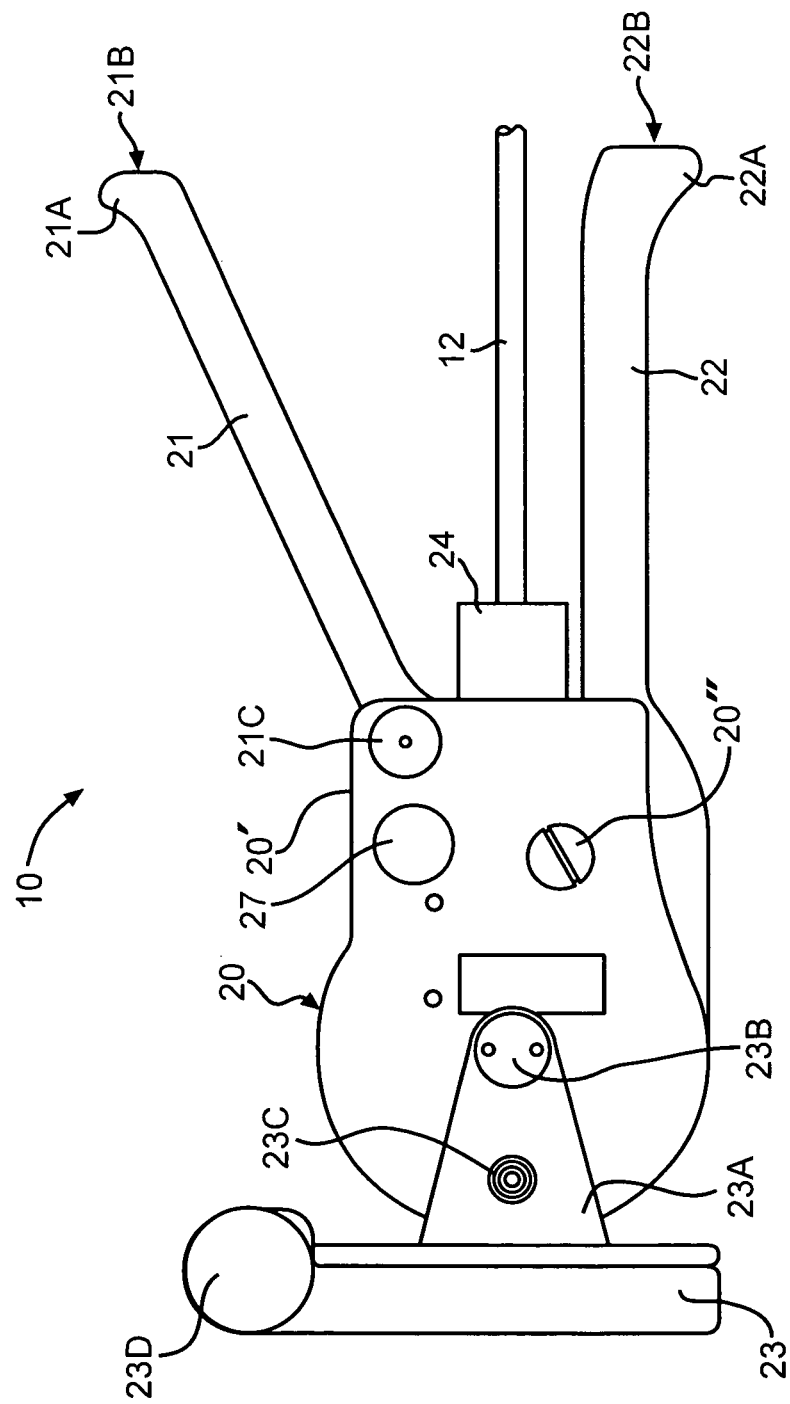
FIG. 6 illustrates the opposite side view of FIG. 5 of the hand grip having the detachable stylet mounted thereto.

In an exemplary embodiment as shown in FIGS. 1, 2, and 4A-4D hand grip 20 comprises a display means 23. Display means 23 can be pivotably mounted on hand grip 20 to allow for rotation to a desired viewing position. Display means 23 can be any viewing monitor such as an LCD screen. As shown in FIG. 1, display means 23 pivots towards medical professional M for better viewing. FIGS. 4C and 4D are side views of device 10 with monitor 23 in opposite configurations illustrating that the monitor can rotate or pivot approximately 180 degrees. FIG. 4B shows the trigger 21 and articulation section 13 in an actuated state of trigger 21' and articulation 13', i.e., curved when trigger 21 is squeezed towards stationary handle 22 of handgrip 20 and represented in dotted lines. As shown in FIG. 2 and FIG. 6, in an exemplary embodiment, display means 23 is connected to a base extension 23A which connects to hand grip 20 on pivot point 23B. Pivot point 23B can be any means for providing a desired pivot such as a screw or bolt. In a particular embodiment base extension 23A is constructed to define a substantially triangular geometry thus providing adequate support for the monitor and convenient pivoting along pivot point 23B.

In an exemplary embodiment, detachable stylet 11 comprises an electrical connection 26 illustrated in FIG. 3A. Electrical connection 26 provides a port and connection to a camera having a lens 28 (schematically shown in FIG. 4E) mounted in the tip 112. In a particular embodiment, the camera is a CMOS chip having optics. Electrical connection 26 is adapted to receive a mating connector mounted inside of hand grip 20. Connecting stylet 11 to handgrip 20 allows for connection of camera 28 to display means 23 via electrical connection 26. The camera is connected to electrical connection 26 through one or more wires that run through the interior length of elongated tube 12. When connected or coupled to each other, display means 23 can display a pathway through the trachea via the camera. This provides for convenient steering and guidance for the medical professional to direct the tube into a desired location.

Typically, stylet 11 is disinfected in a disinfecting fluid prior to use. Submerging stylet 11 in a liquid for any period of time can damage any of the electrical components, including electrical connection port 26 and the camera. Thus, in an exemplary embodiment, device 11 comprises a soak cap 27. Soak cap 27 is adapted to protectively mount over and around electrical connection port 26. Exposure to liquid is substantially prevented when soak cap 27 is mounted over connection port 26 thus allowing for convenient disinfection of stylet 11. If stylet 11 is submerged in a disinfection liquid, the electrical components are protected by soak cap 27. Typically, soak cap 27 is mounted on one side of hand grip 20 as shown in FIG. 2. Soak cap 27 rests on the outer surface of hand grip 20 until it is needed to cover the electrical connection 26 of stylet 11 as shown in FIG. 3A. Typically electrical connection 26 faces perpendicular to axis A-A on interior face 17B of housing 14. In a particular embodiment, soak cap 27 lies flush with face 17B when mounted over electrical connection 26.

Figure 5:
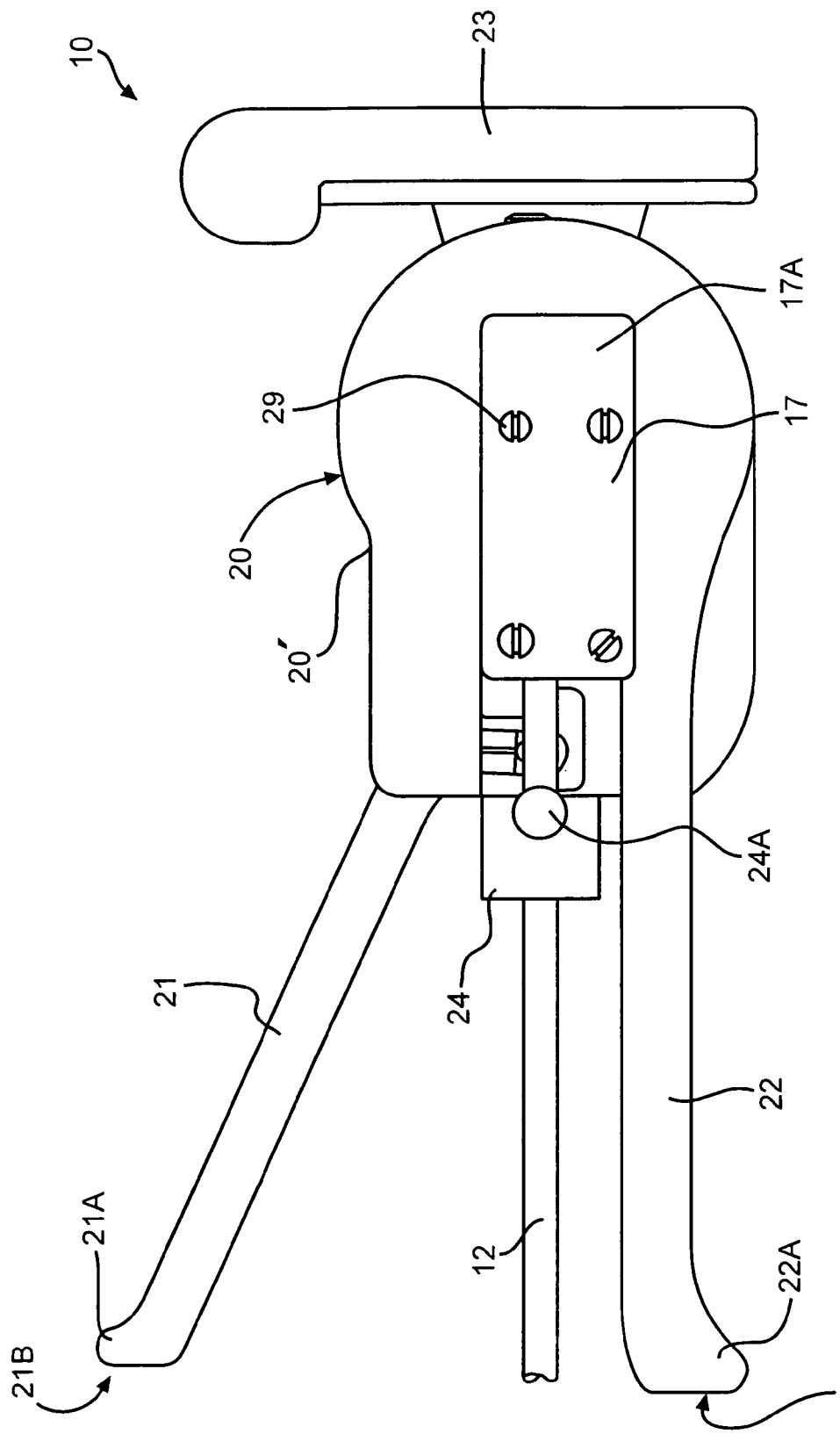
FIG. 5 illustrates a close-up view of the detachable stylet mounted in the hand grip of FIGS. 3A and 3B.
Figure 7:
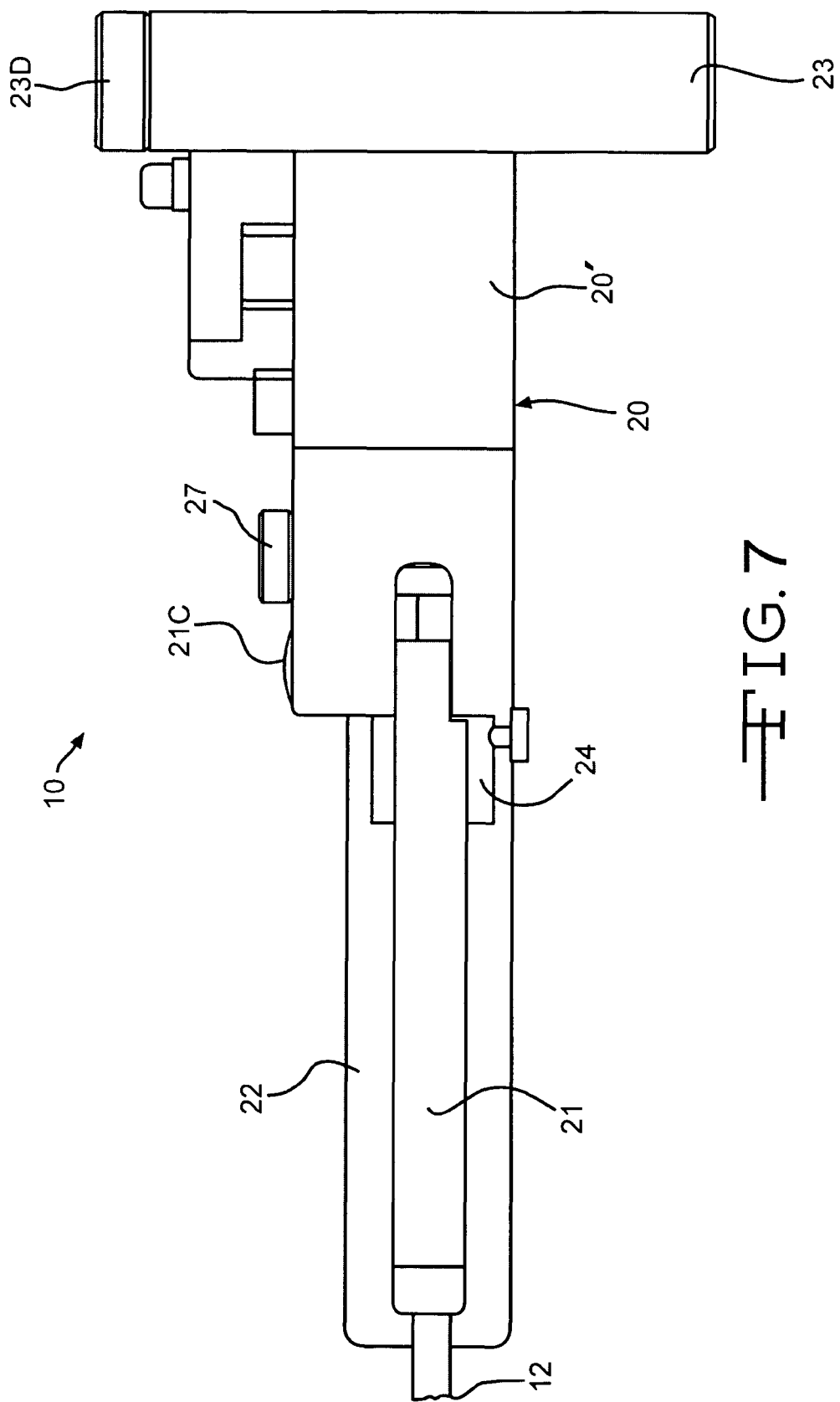
FIG. 7 illustrates a trigger side view of the device of FIG. 1.

FIGS. 5-7 illustrate magnified opposite side views and a trigger side view of hand grip 20 having display means 23 and mounted to stylet 11. Actuator housing 14 forms an enclosure around the actuator assembly and proximal end of elongated tube 12. In a particular embodiment, back plate 17 is mounted onto housing 14 by several mounting features 29 such as screws or bolts. Hand grip 20 comprises: (i) a grip housing 20', (ii) a trigger 21 as a pivotable lever extending from housing 20' towards distal end 12B of elongated tube 12 and away and nonparallel with respect to longitudinal axis A-A; and (iii) a stationary handle 22 as base for squeezing trigger 21 towards handle 22 when engaged. Base handle 22 extends towards distal end 12B and parallel with respect to axis A-A. Trigger 21 is mounted onto housing 20' on a pivot feature 21C.

In an exemplary embodiment, trigger 21 and handle 22 each define a curving lip 21A and 22A at distal ends 21B and 22B, respectively. Lips 21A and 22A serve as terminating ends of trigger 21 and handle 22 such that a user can conveniently feel where to properly place his hand when using device 10. Although shown as terminating ends, lips 21A and 22A can be located anywhere along their respective structure since their intention is to provide indication to a particular hand position. Lips 21A and 22A also serve as structural stops to substantially deter slipping of the hand. Typically lips 21A and 22A face away from each other.

FIG. 6 illustrates an opposite side view of FIG. 5 of hand grip 20 with display means 23 mounted thereon. In a particular embodiment, display means 23 is mounted on a pivotable extension 23A on a pivot point 23B. In a particular embodiment, a video-out port 23C is mounted on extension 23A. Typically, port 23C is an RCA composite port adapted to allow for coupling or connection to an external display means or monitor such as a computer or LCD screen. Display means 23 can further comprise a power source 23D such as a battery. Housing 20' can be securely held together by a securing means 20" such as a screw or bolt.

Figure 8:
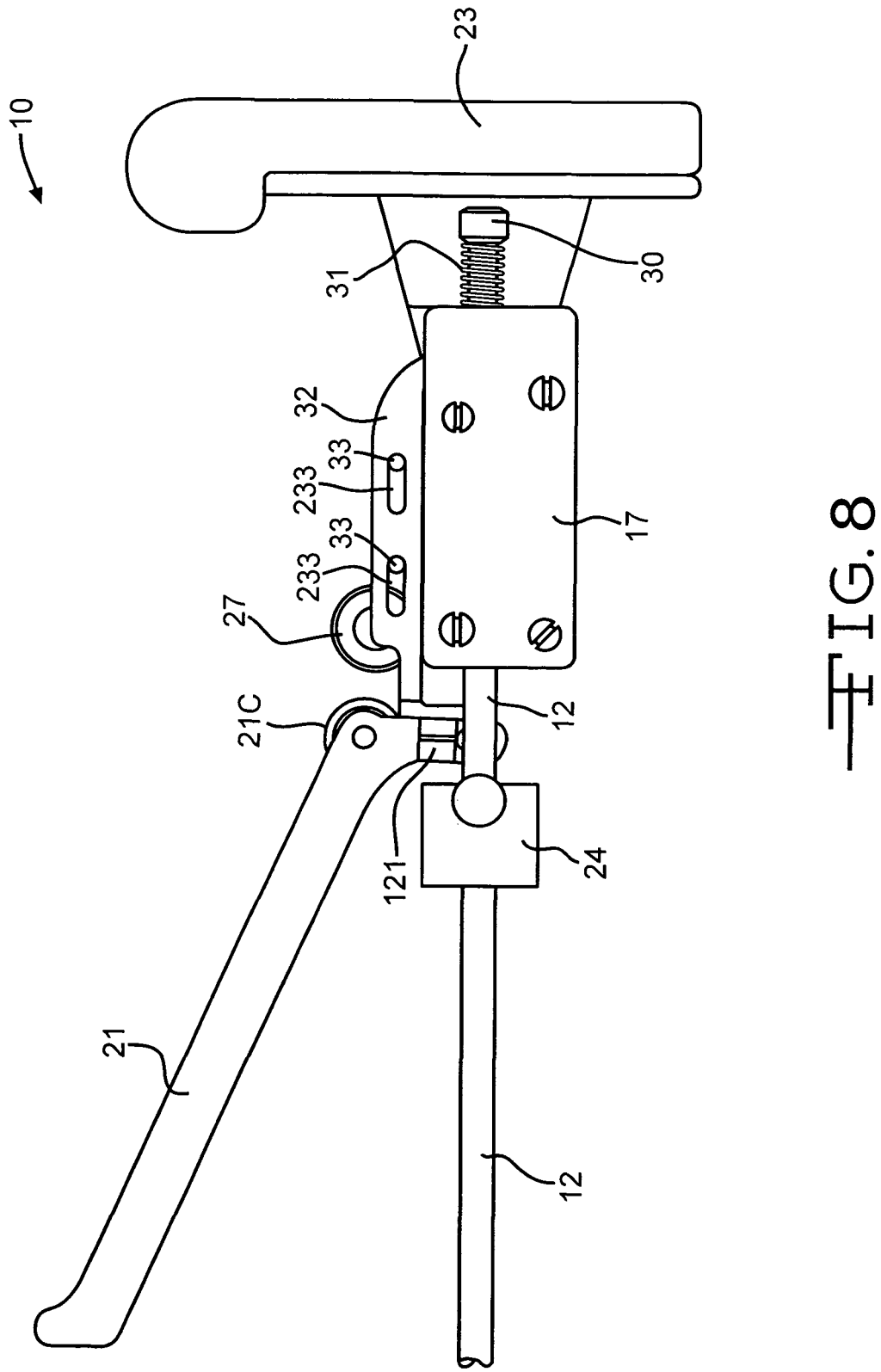
FIG. 8 illustrates a side view with the grip housing removed from the device of FIG. 1.
Figure 9:
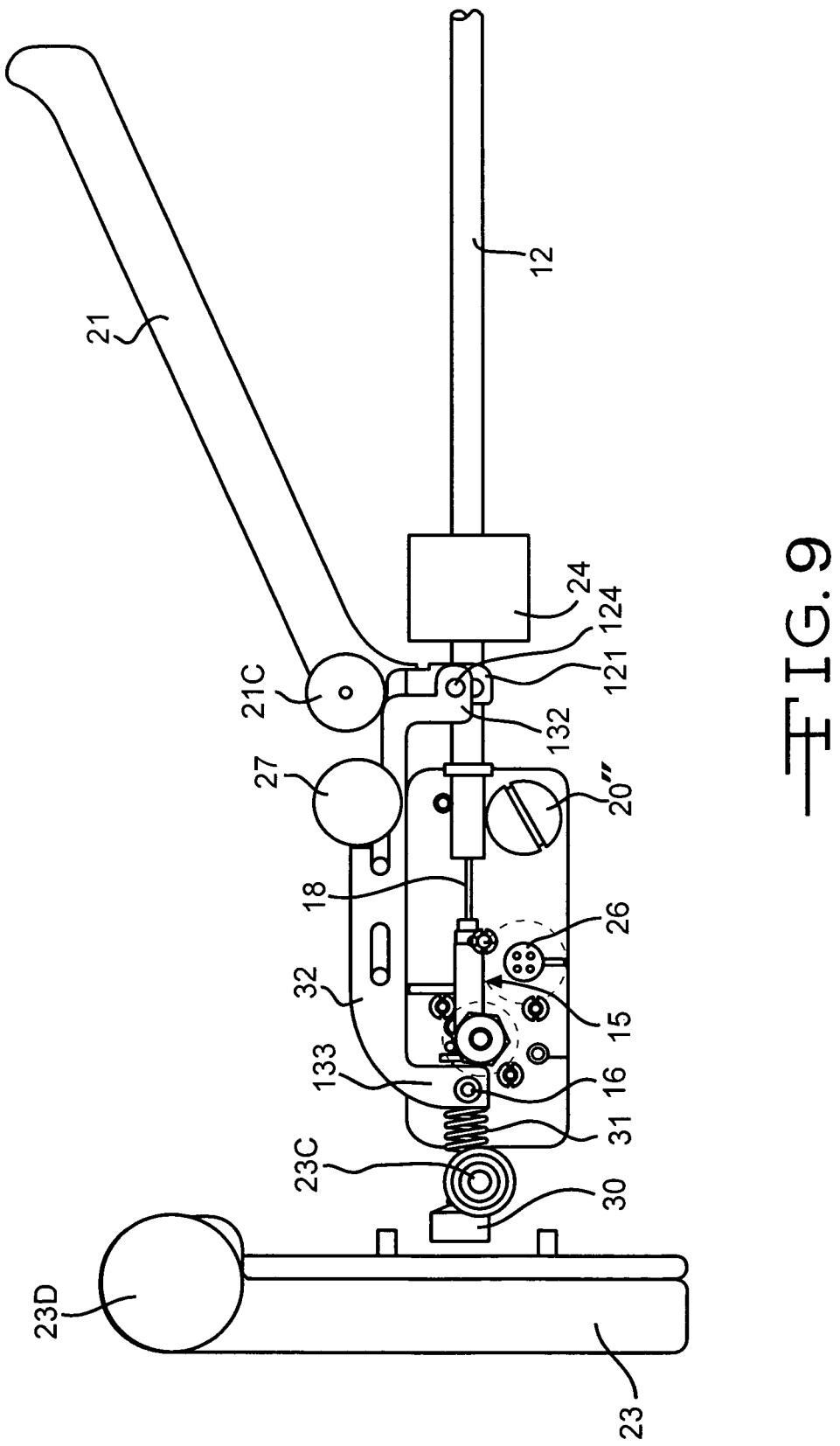
FIG. 9 illustrates an opposite side view of FIG. 8 with the internal components exposed showing the actuator assembly.

FIGS. 8-17 illustrate various exploded views of the internal components of both hand grip 20 and actuator assembly 15. FIG. 8 illustrates a side view from the stylet 11 side of device 10 with the grip housing 20' removed. FIG. 9 illustrates device 10 with the grip housing 20' and actuator housing 14 removed from the opposite side of FIG. 8. Trigger 21 is connected to a lever member 121 at pivot feature 21C. Lever member 121 extends substantially perpendicular to the axis A-A and defines an opening 122. In an exemplary embodiment, opening 122 defines an oblong geometry to all for sliding of the lever member during squeezing, i.e. actuation, of the trigger 21.

Figure 10:
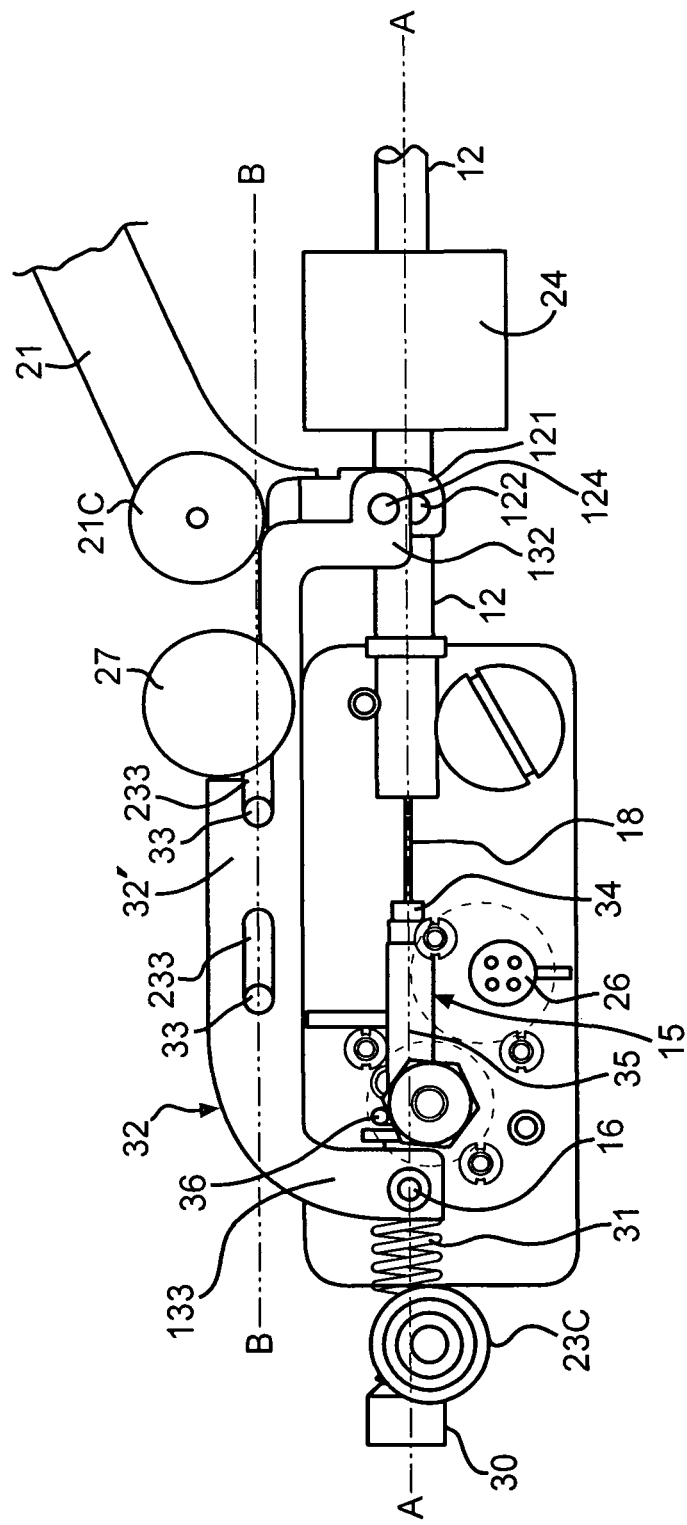
FIG. 10 illustrates a close-up view of the actuator assembly in connection with the trigger mechanism.

Trigger 21 engages connector linkage 32 through opening 122 of lever member 121 by a pin 124. Connector linkage 32 includes a distal end 132 and a proximal end 133. The distal end connects to trigger 21 through a connection means, such as a pin, screw, or bolt, in opening 122. As shown in FIG. 10, linkage 32 includes an elongated back bone 32' that extends along a longitudinal axis B-B which is parallel with axis A-A. Extending perpendicular to axis B-B are distal end 132 and proximal end 133. Back bone 32' defines a pair of guidance openings 233. Openings 233 are substantially elongated ovals that receive guide pins 33. Guide pins 33 are mounted on the inner surface of grip housing 20' and extend through the openings 233. Pins 33 provide structural guidance to linkage 32 during actuation. Typically, when trigger 21 is squeezed towards base handle 22, lever member 121 pivots to apply force to linkage 32 at the connection at distal end 132. Linkage 32 is connected to lever member 121 through a pin 124 in opening 122. Linkage 32 translates along the A-A axis away from elongated tube 12. Guide pins 33 provide structural support to linkage 32 and thus backbone 32' translates along axis B-B. A coil spring 31 is positioned between proximal end 133 of linkage 32 and support stop 30. The spring is operable to return linkage 32 and thus trigger 21 back to resting position when the force on the trigger is removed.

FIGS. 9-14 illustrate the internal components of actuator assembly 15. Connection means 16 is part of actuator assembly 15. In a particular embodiment, actuator assembly 15 is constructed within actuator housing 14 of detachable stylet 11. In a further embodiment, device 10 is constructed as an entire assembly without the detachable feature. Connection means 16 can be any means to secure connection of actuator assembly 15 to linkage 32 such as a stem, protruding pin or bullet shaped extension. Connection means 16 engages a hole or opening defined in proximal end 133 of linkage 32. Connection means is attached to a plunger 34 that slides within a chamber 35. Chamber 35 abuts against a seal 36 to prevent liquid contamination during actuation. Plunger 34 is connected to control wire 18. During actuation, i.e., trigger 21 is being squeezed, lever 121 acts upon linkage 32 which translates away from trigger 21. As linkage 32 compresses spring 31, it acts upon connector means 16 which pulls plunger 34 to translate through chamber 35. Plunger 34 pulls control wire 18 which then causes tube 12 to curve at the articulation section 13. This mechanism provides a user with controlled curving and movement through the squeezing of trigger 21.

Figure 11:
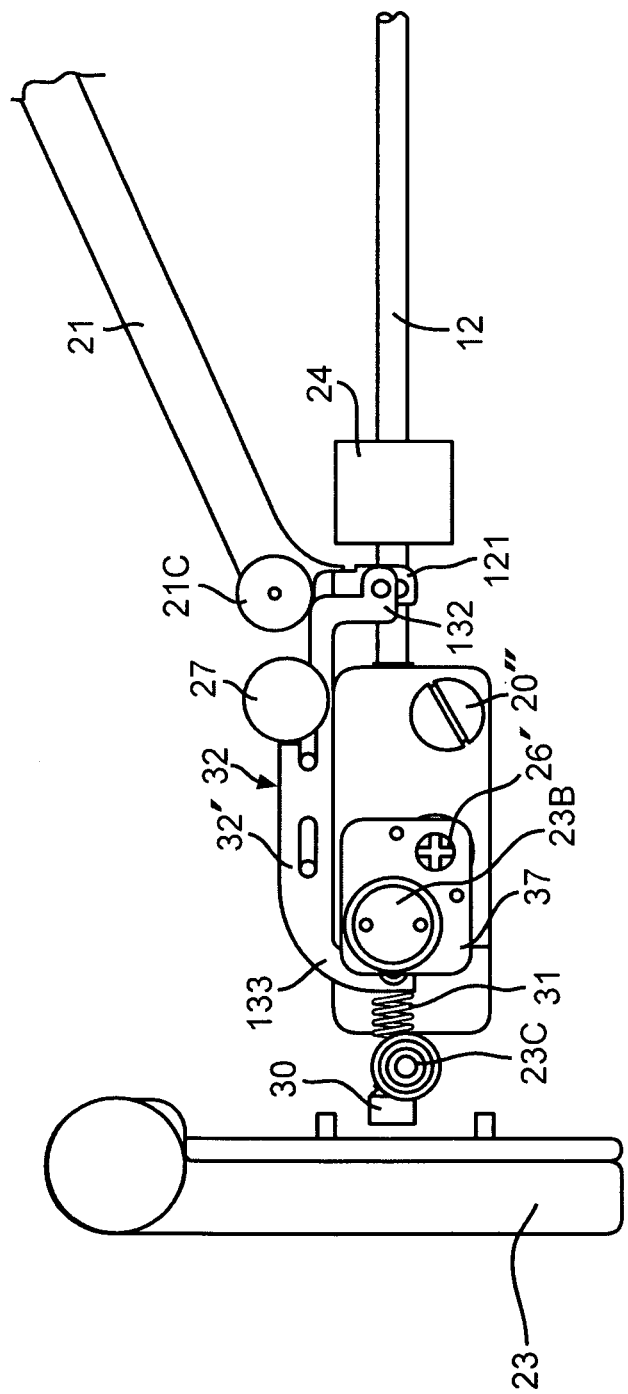
FIG. 11 illustrates then internal components of the device of FIG. 1 with the retaining plate.
Figure 12:
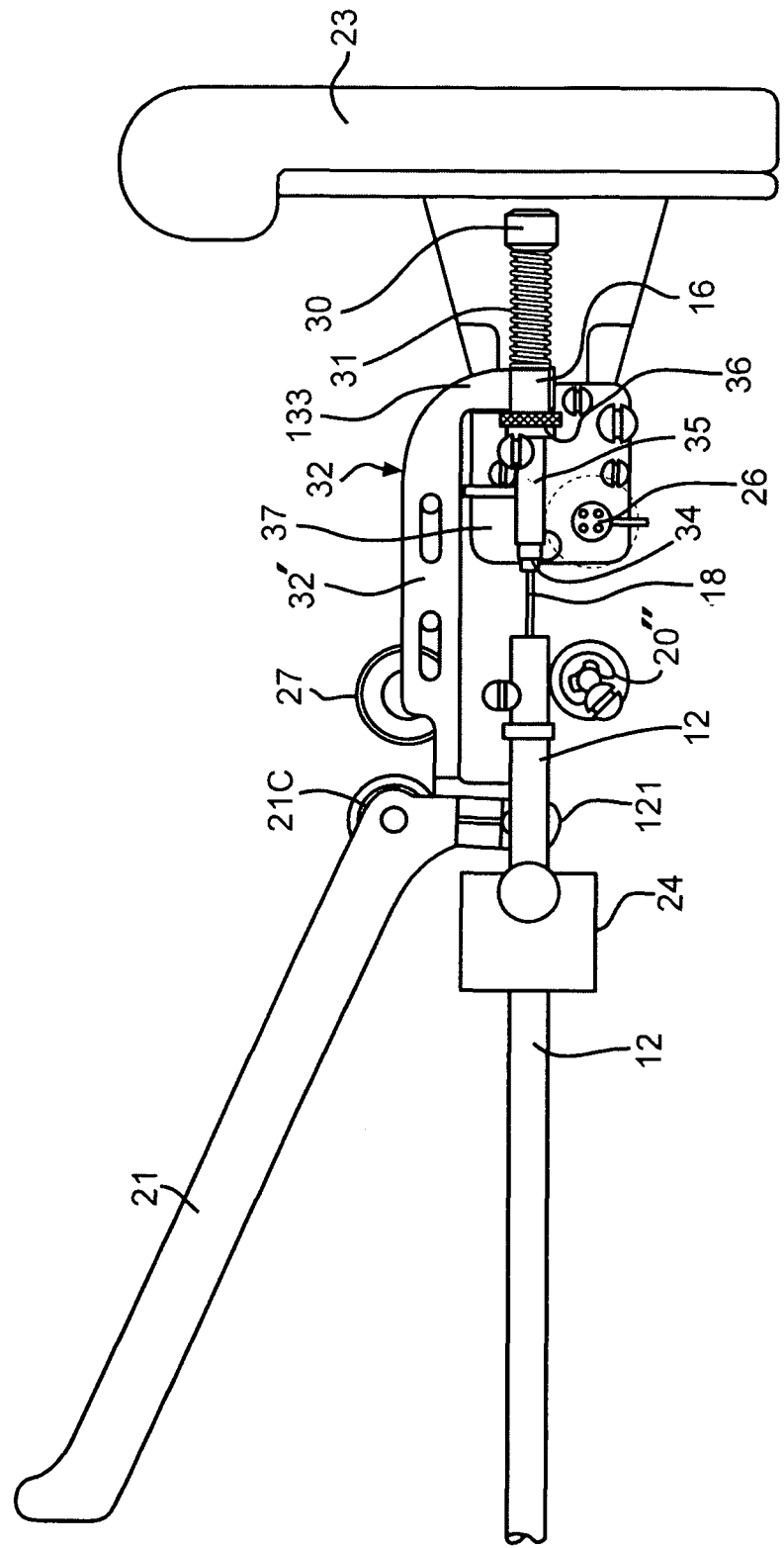
FIG. 12 illustrates the actuator assembly from the side of the stylet engaged with the trigger mechanism.
Figure 13:
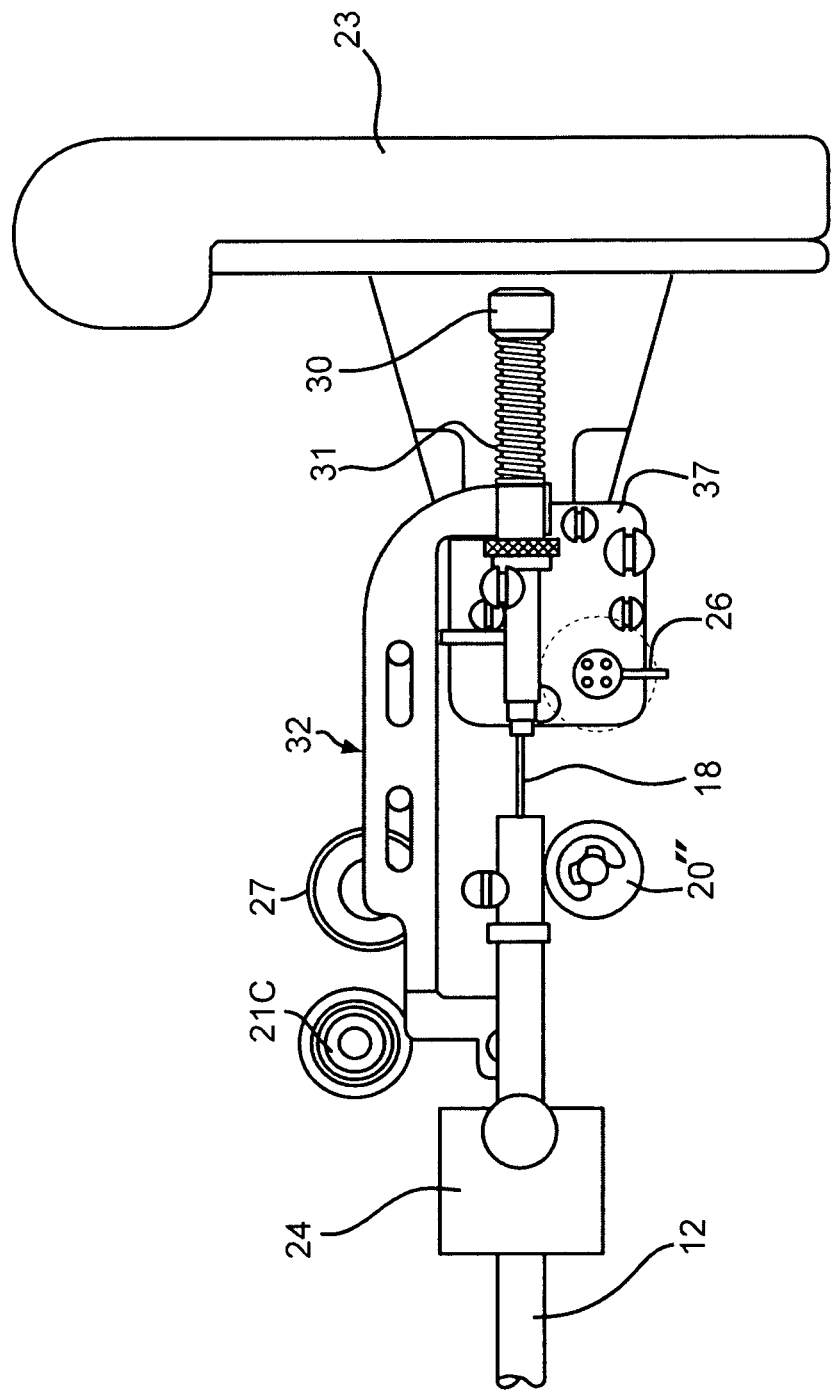
FIG. 13 illustrates a close-up view of the actuator assembly of FIG. 12 with the trigger removed.
Figure 14:
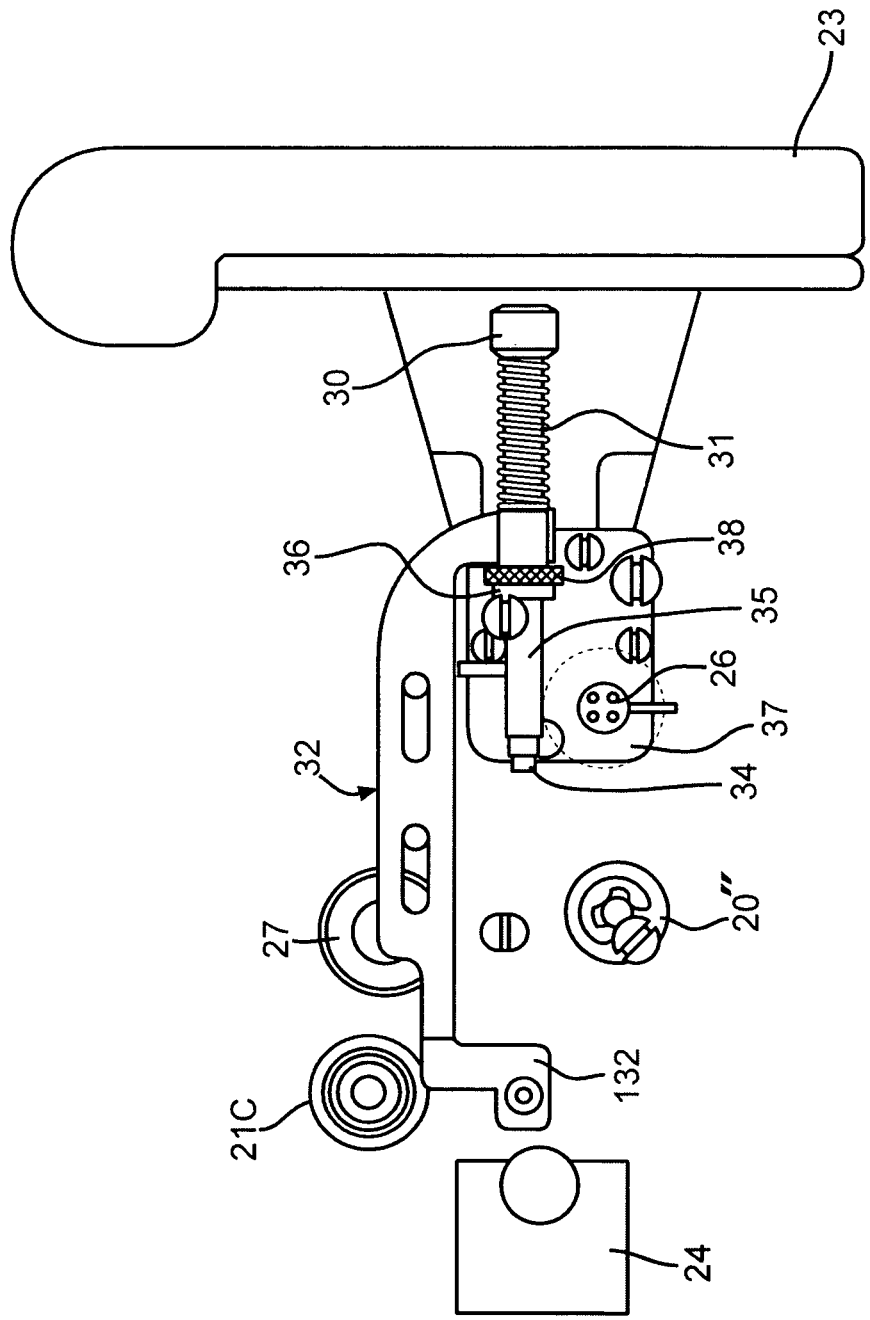
FIG. 14 illustrates the view of FIG. 13 with the control wire and elongated tube removed.
Figure 15:
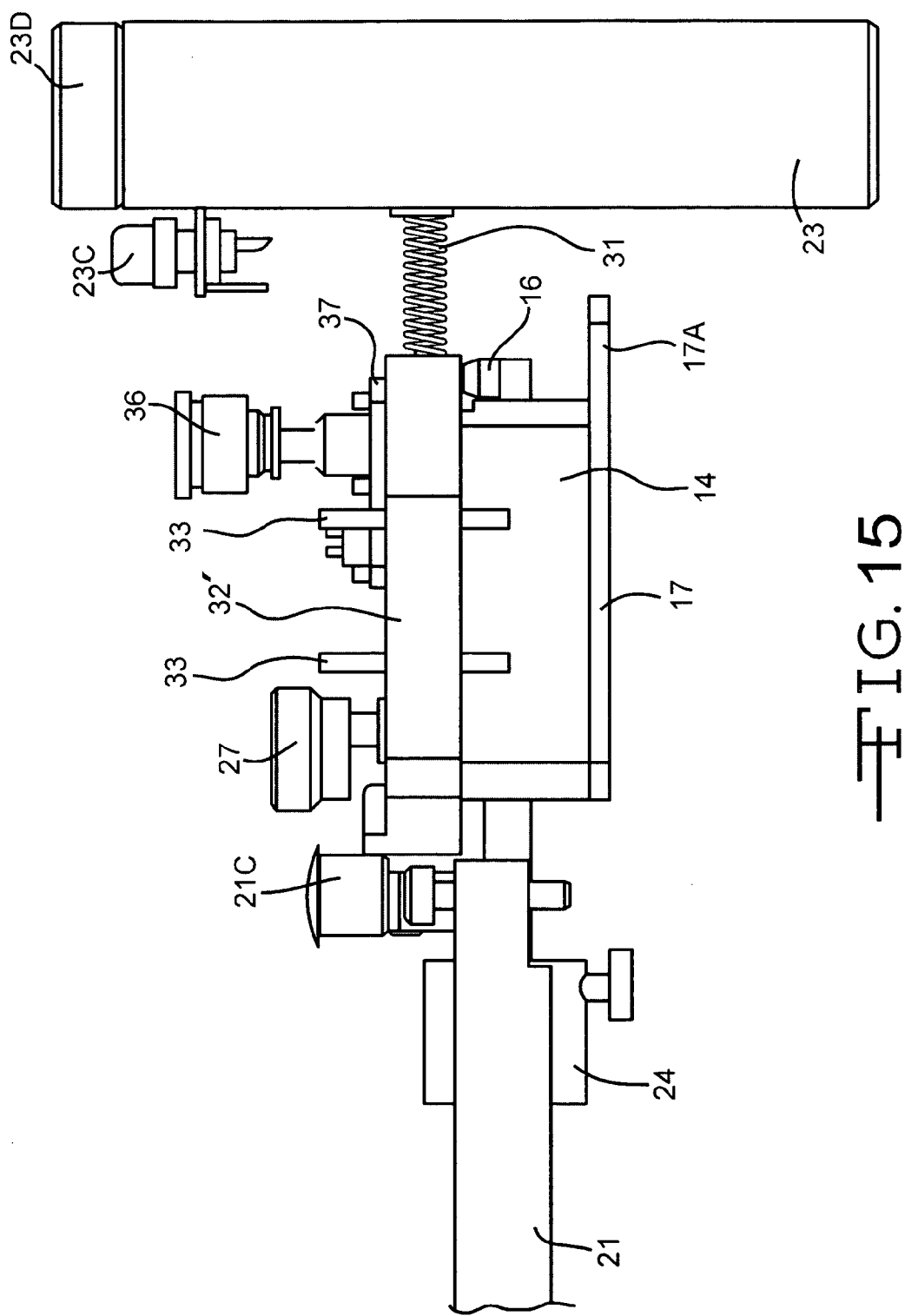
FIG. 15 illustrates a trigger side view of the actuator assembly engaged with the trigger mechanism with the grip housing removed.
Figure 16:
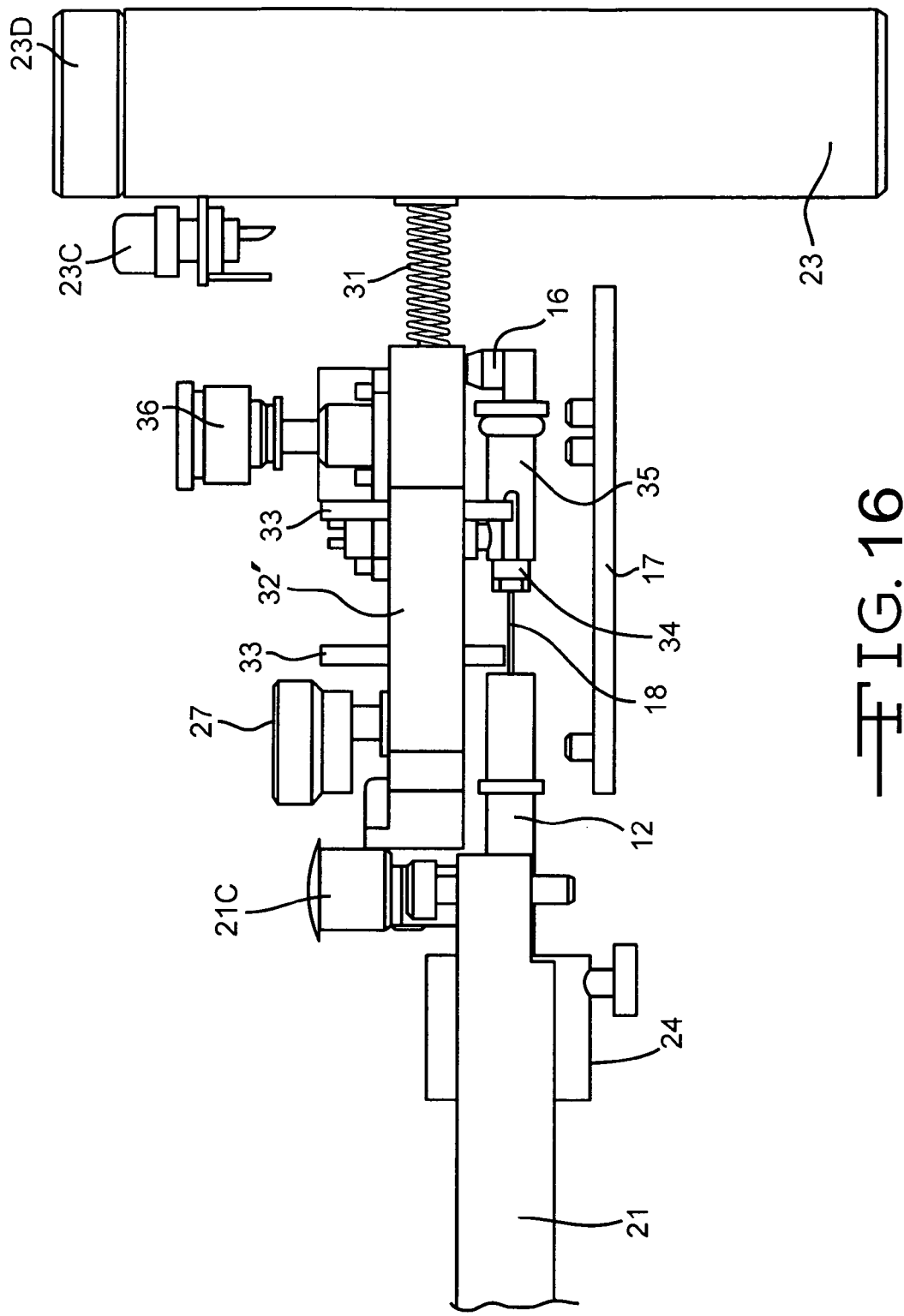
FIG. 16 illustrates a trigger side view of FIG. 15 with the actuator housing removed.
Figure 17:
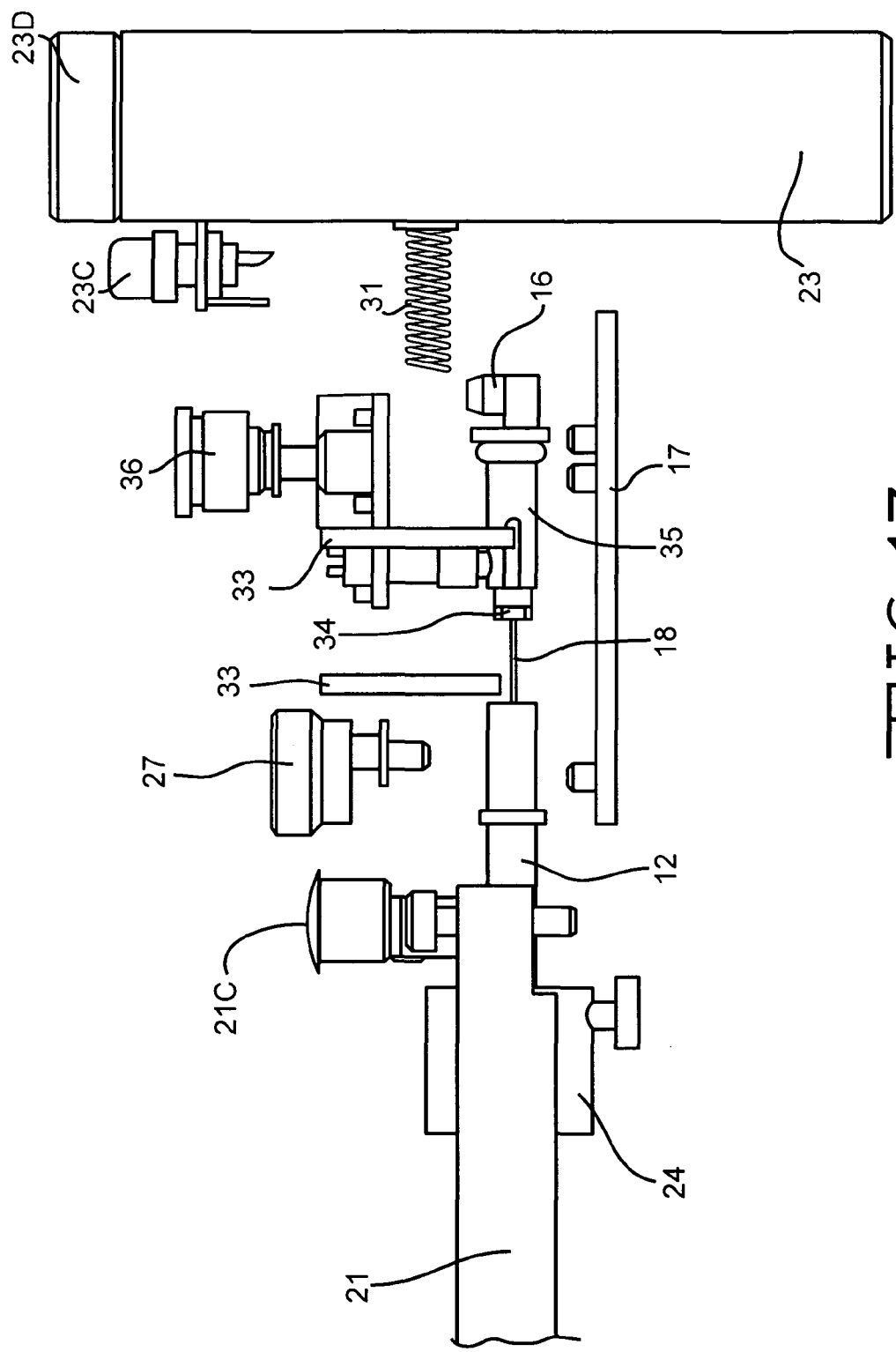
FIG. 17 illustrates a trigger side view of FIG. 16 with the linkage removed.

FIGS. 11-14 illustrate device 10 having a retaining plate 37. Retaining plate 37 is mounted within hand grip 20 and provides structural support for electrical connection 26 and pivot point 23B. Mating electrical connection 26' is shown in FIG. 11 within retaining plate 37 and is adapted to engage electrical connection 26 mounted within actuator housing 14. Seal 36 abuts against seal support 38 which operates as a stop for forming the seal during actuation. FIGS. 15-17 illustrate top views of device 10 with various components removed to illustrate component configuration.

Figure 18:
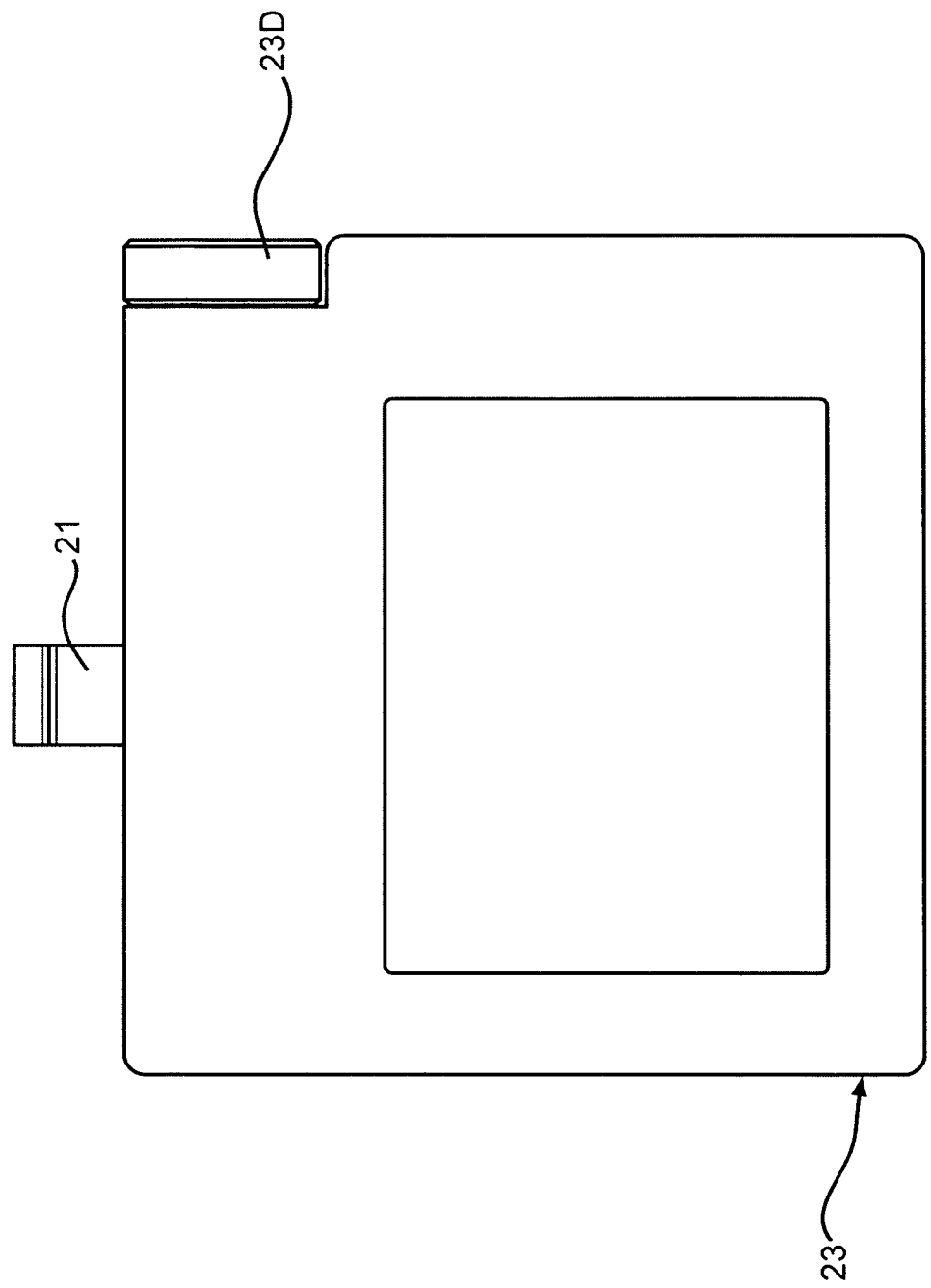
FIG. 18 illustrates an exemplary display means having a monitor and power supply.
Figure 19:
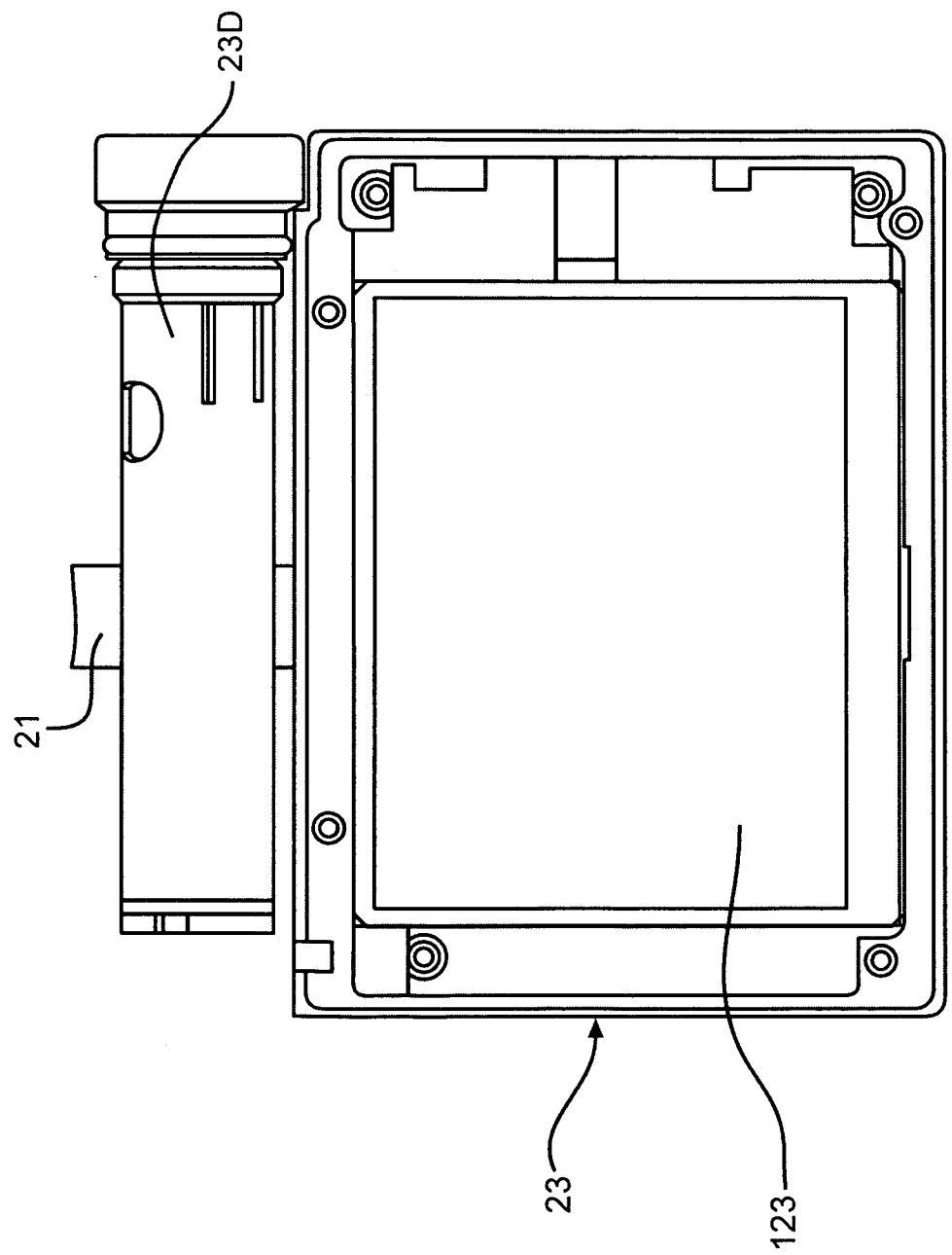
FIG. 19 illustrates the display means of FIG. 18 illustrating internal components.
Figure 20:
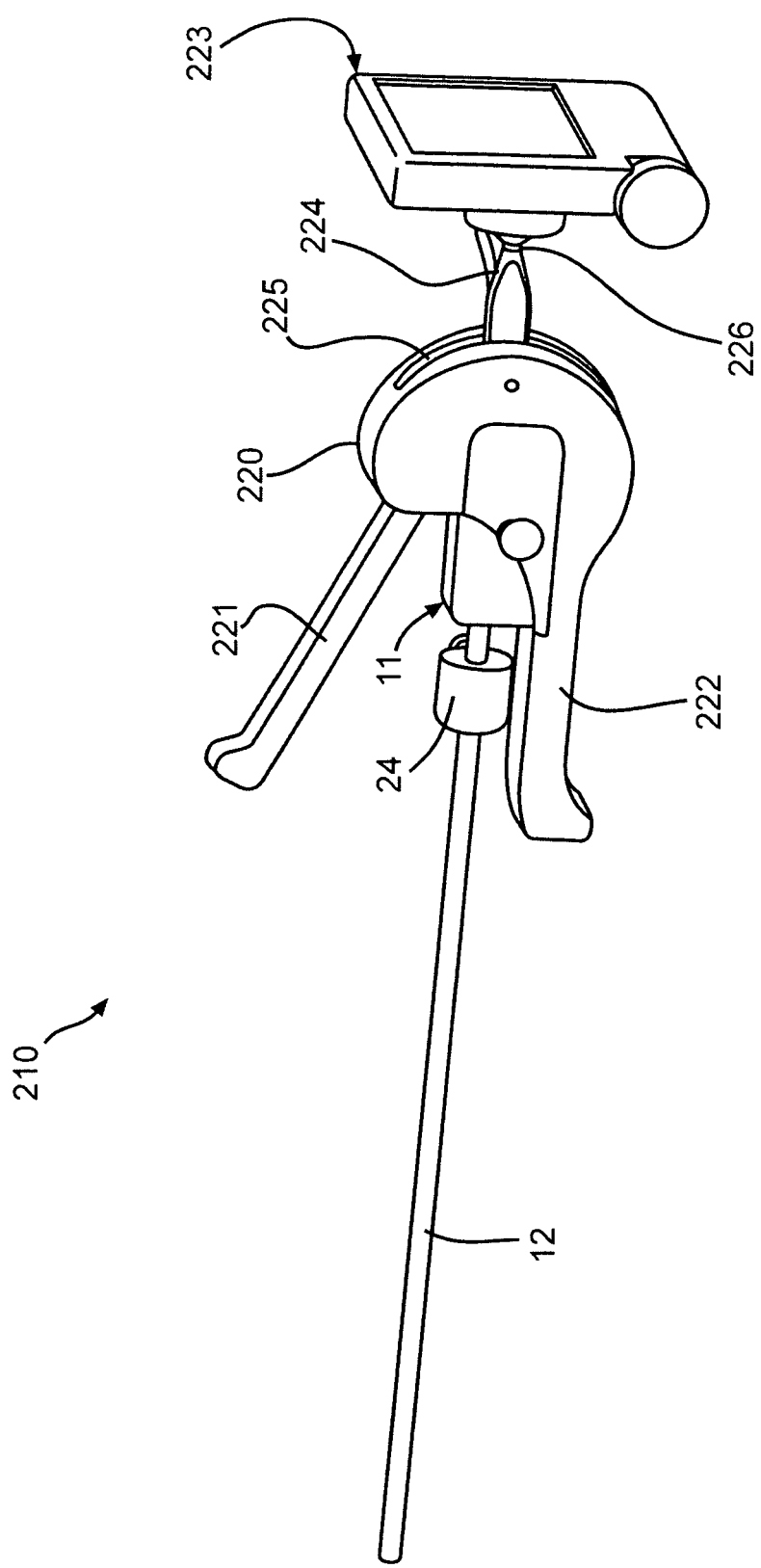
FIG. 20 illustrates an exemplary embodiment of an endotracheal intubation device having a hand grip with display means and trigger engaged with a stylet assembly.
Figure 21:
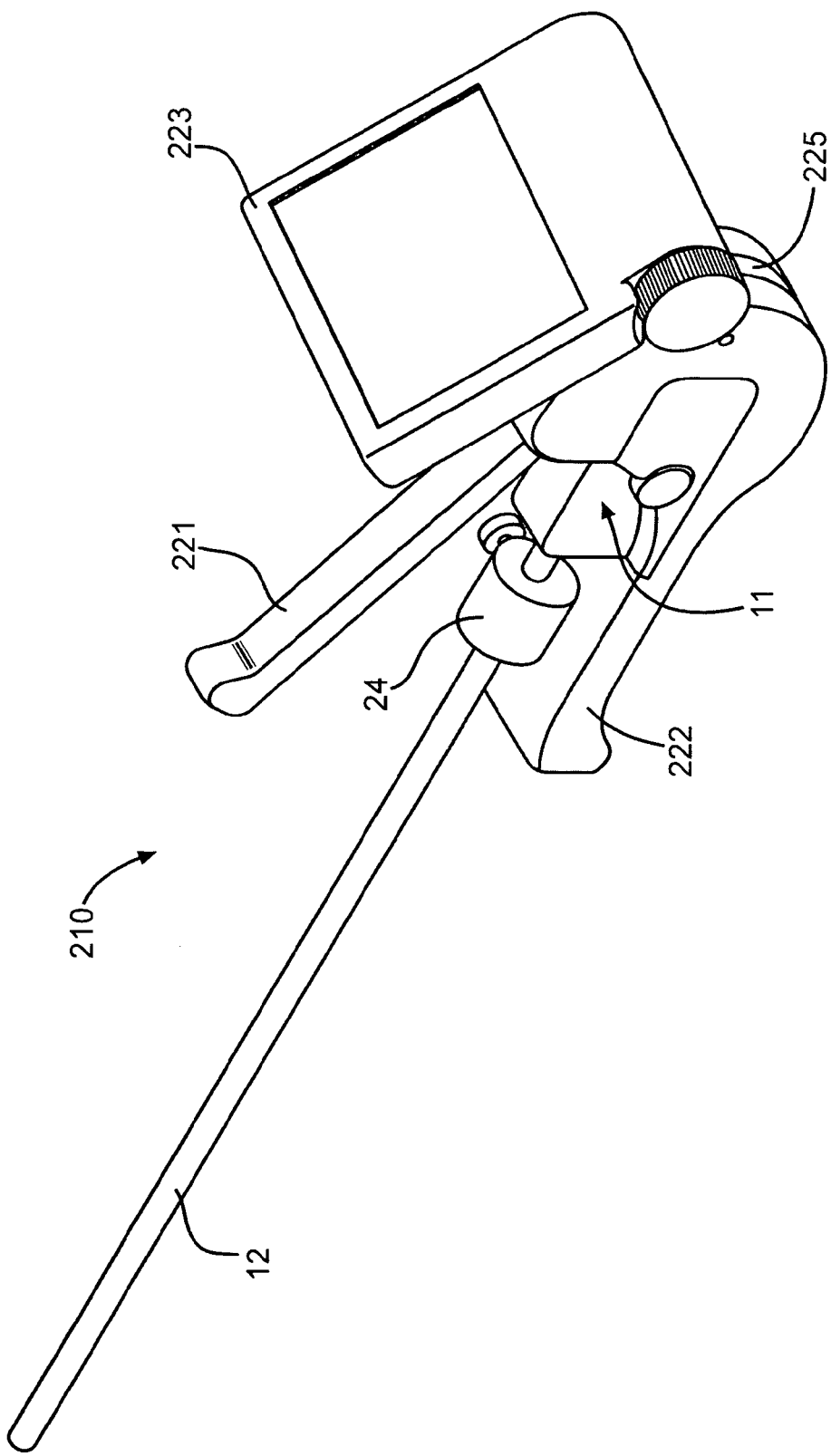
FIG. 21 illustrates the device of FIG. 20 with the display means in a rotated and adjusted orientation.

FIGS. 18-19 illustrate a front view of the display means 23. Display means 23 can be any monitor having a screen 123. In a particular embodiment, monitor 123 is a LCD screen. Display means 23 includes a power source 23D such as a battery. In a particular embodiment, as shown in FIGS. 20-23, a device 210 is provided having hand grip 220, trigger 221, and base handle 222. Hand grip 220 is adapted to attach to a detachable stylet 11 and function in the same manner as previously described with respect to hand grip 20 above. Hand grip 220 defines a monitor rotation slot 225 adapted to allow for rotating of display means 223. Display means 223 is mounted on a swivel point 226 of a rotating arm 224. Swivel point 226 allows for a user to position display means 223 in a variety of desired orientations. The rotation through slot 225 in combination with the swivel point 226 provides for convenient repositioning of display means 223 for optimal viewing angles. FIGS. 21 and 22 illustrate exemplary positions of display means 223 with respect to hand grip 220.

In an exemplary embodiment, the video signal from the display means is broadcast wirelessly. The handle functions as a grounding plate for the dipole antenna of the wireless transmitter. The user can function as a grounding plate and thus facilitating clarity of the wireless signal to the receiver.

FIGS. 23A-28C illustrate further particular exemplary embodiments of endotracheal intubation devices with a stylet, hand grip, and display monitor according to the present disclosure. Like numerals are used to describe like features with respect to the embodiments described in FIGS. 1-22. Any differences from those embodiments are described below.

Figures 23A, 23B:
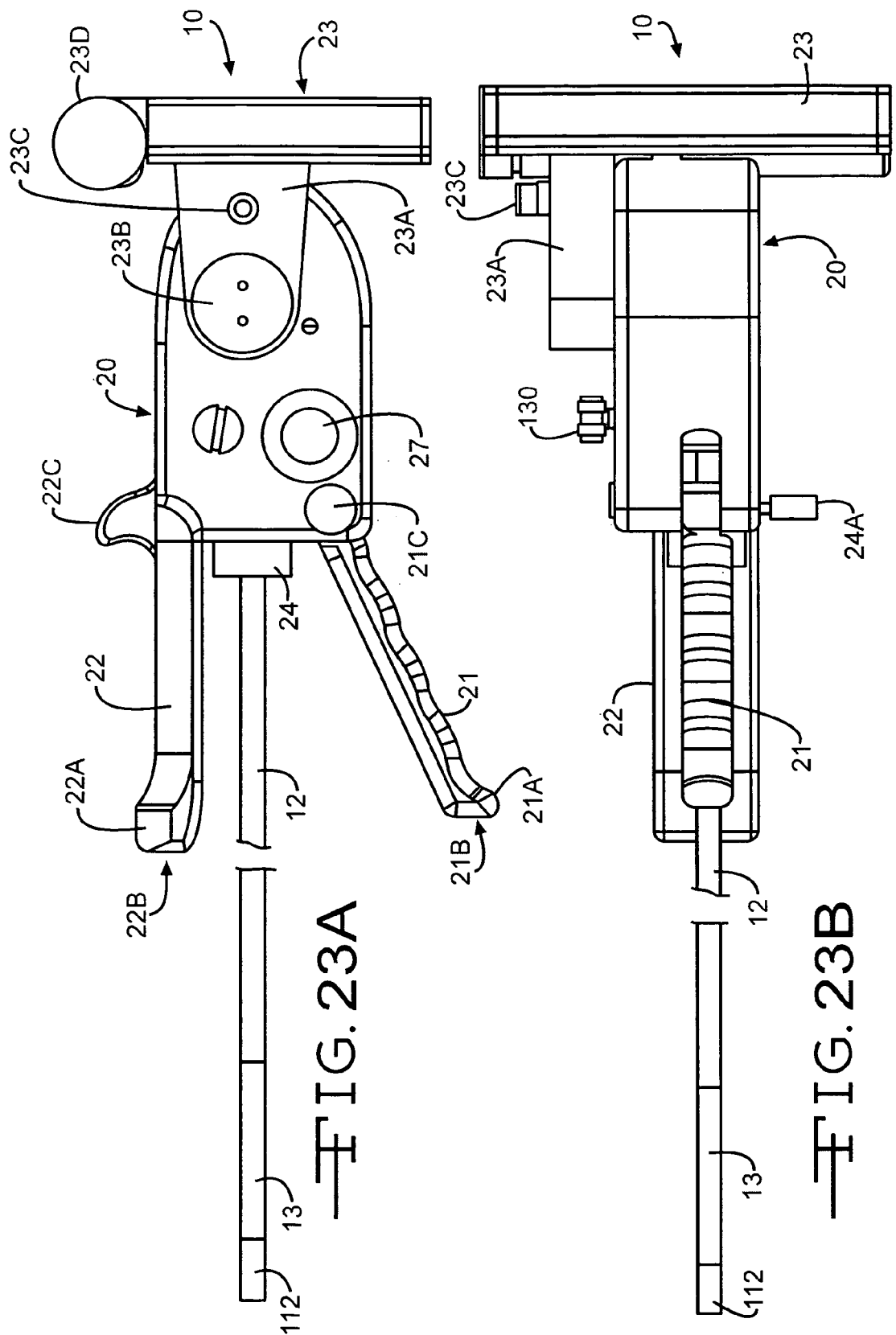

FIGS. 23A-23D illustrate an exemplary endotracheal intubation device 10 having a hand grip 20 with a trigger 21 for convenient articulation of an articulation section 13. FIG. 23A illustrates a first side view of endotracheal intubation device 10 showing a pivot mount 23A for monitor 23. Monitor 23 is connected to grip housing 20 via pivot mount 23A. Pivot mount 23A allows for manual pivoting of monitor 23 about pivot point 23B. The pivot mount 23A is mounted on one side of grip housing 20.

Device 10 can be operated by a medical professional to access patient trachea or allow for viewing of the vocal chords and trachea. FIG. 23B illustrates a trigger side or bottom side view of device 10. FIG. 23C illustrates a stylet side view showing the engagement of stylet assembly 11 with grip housing 20. FIG. 23D illustrates a front view showing monitor 23 and trigger 21 extending away and upwardly at an angle with respect to monitor 23. Monitor 23 comprises a display means 123 and a power source 23D. Display means 123 can be any visual display technology such as a liquid crystal display (LCD). Typically, power source 23D is comprised of lead acid or lithium ion batteries. In a particular embodiment, monitor 23 comprises a low battery light indicator 324, typically an LED. Monitor 23 is in electrical connection with stylet 11 through electrical connection 26 (FIG. 24B). Electrical connection 26 is coupled through electrical wires to a camera mounted in a tip portion 112 of stylet 11. The camera comprises an external lens 28 shown in the distal tip view of FIG. 24G. Typically lens 28 is mounted adjacent at least one, but often two LEDs 19 to provide light in use. The camera allows for the medical professional to view the pathway into the patient via the monitor 123. This allows for more accurate tube 12 placement of the stylet assembly 11 and for avoiding damage to sensitive and crucial anatomy such as the vocal chords.

Figure 27A:
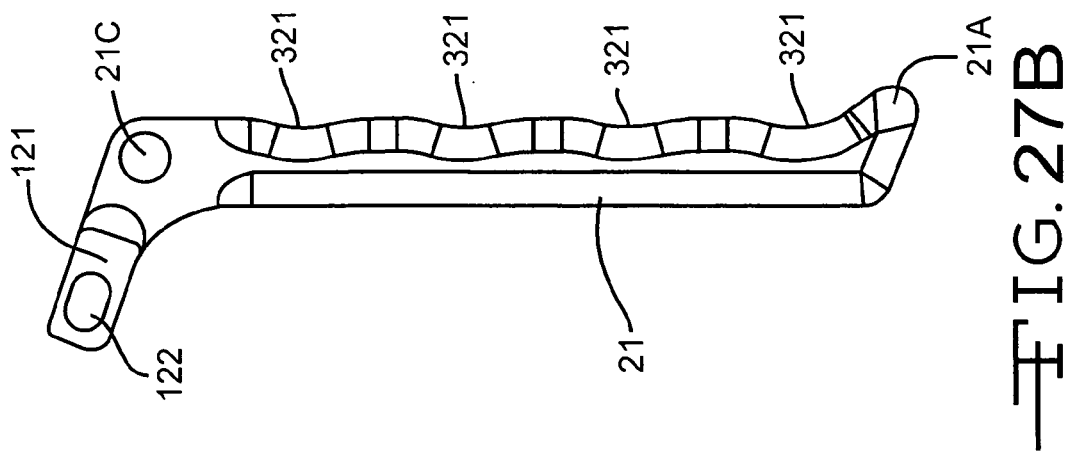
FIG. 27A illustrates a perspective view of an exemplary grip housing without the trigger connected.
Figure 27B:
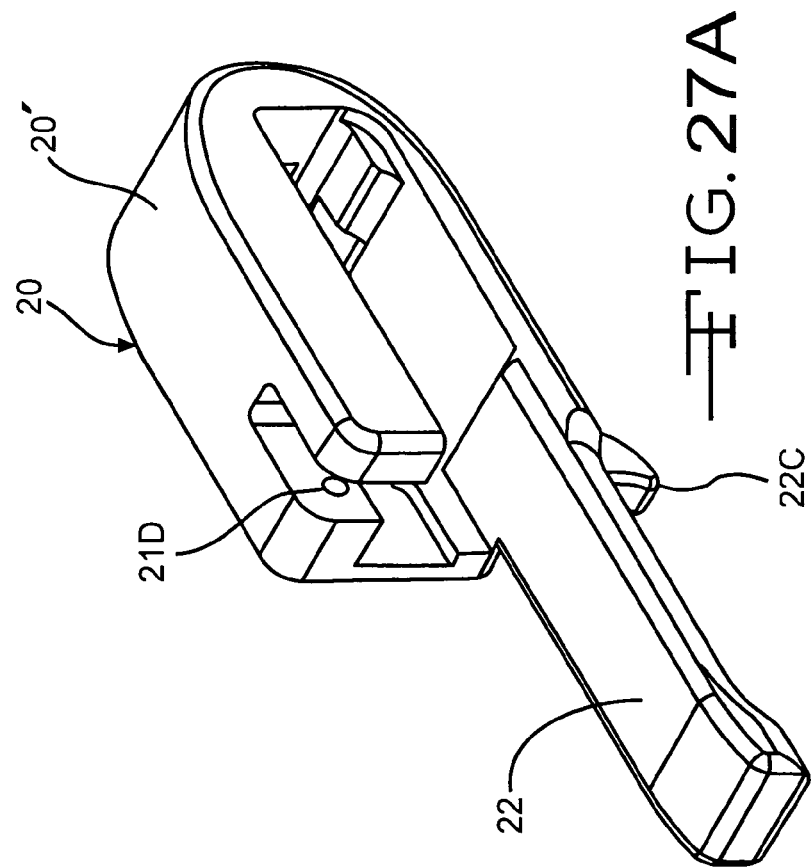
FIG. 27B illustrates an exemplary trigger with finger grooves.

FIGS. 25A-25C illustrate hand grip 20 detached from stylet assembly 11. Grip 20 comprises a trigger 21 which pivots about a pivot pin 21C (FIG. 25C). Grip 20 defines a pair of receiving holes 21D (FIG. 27A) for receiving pin 21C. This allows for trigger 21 to pivot about pin 21C when squeezed. A stand alone trigger 21 is shown in FIG. 27B. Trigger 21 includes finger grooves 321 for easy and effective gripping. Hand grip 20 includes a stationary handle 22 as a base. Base handle 22 extends away from housing 20 to provide a gripping means for a user. Typically, a medical professional can place his hand against base 22 while wrapping his fingers around the pivotable trigger 21. Trigger 21 is connected to housing 20 such that it retracts away from base 22 while at rest.

Trigger 21 is connected to hand grip 20 through pin 21C. Trigger 21 comprises a lever member 121. Lever 121 extends at an angle from pivot pin 21C inside hand grip 20. A cam 122 is defined on lever 121 (See FIG. 27B) which allows for connection to linkage 32 (FIG. 28A) through a translating pin 124. Cam 122 receives pin 124 which connects to linkage 32 at pin hole 323 (FIGS. 28A-28C). When trigger 21 is squeezed, pin 124 moves within cam 122 and translates linkage 32 linearly towards monitor 23 along axis B-B (FIG. 28B). Linkage 32 can also be referred to as a bolt. A spring 31 (shown in cross section view A-A of housing 20 in FIG. 26A) abuts against linkage 32 in a spring cavity 331. Typically spring 31 is a coil spring and returns trigger 21 to its original rest position once a squeezing force is removed. Spring 31 abuts against a stop 30 mounted within grip 20 (See FIG. 26A).

Base handle 22 comprises an upper stop 22C. Stop 22C extends perpendicular to an axis defined by handle 22. Typically, stop 22C also curves slightly thereby substantially resembling a shark fin geometry as shown in the side view of FIG. 25C. The stop 22C is detectable to the touch and slightly forms around the hand of the user's grip. The fin configuration substantially prevents unintended slippage. Moreover, the stop 22C can serve as an anchor or abutment for the user to secure his grip while pulling on trigger 21.

In an exemplary embodiment, device 10 comprises a detachable stylet assembly 11 as shown detached in FIGS. 24A-24C. Stylet 11 is comprised of an elongated tube 12 extending from actuator housing 14. Stylet 11 can also be referred to as a "working length" and is adapted to connect into hand grip 20. Typically, stylet 11 snaps into place in hand grip 20 but can also be secured by a screw 130 as shown in FIG. 25C. When mounted in grip 20, electrical connection 26 is coupled to a receiving section in grip 20 and forms an electrical connection between the camera and monitor 23.

FIG. 24A illustrates a perspective view of stylet 11. Stylet assembly 11 is adapted to connect with a hand grip 20 as shown in FIG. 23C. Elongated tube 12 defines a proximal end 12A for detachably mounting the stylet to hand grip 20, and a distal end 12B for entering the trachea of a patient. Tube 12 comprises an articulation section 13 adjacent distal end 12B. Section 13 is adapted to curve into a trachea upon actuation of trigger 21 from hand grip 20. The hand grip 20 comprises a trigger 21 that is squeezed by a professional to actuate section 13. Mounted on tube 12 is a tube stop 24 (FIGS. 24A-24C, 24F) comprising an adjustment knob 24A and adapted to allow for adjustable mounting of an endotracheal tube 25 over and around the elongated tube 12. In a particular embodiment, device 10 is used to insert and place an endotracheal tube into the patient to clear the trachea and then device 10 is subsequently removed leaving the endotracheal tube (not shown) in place for further procedures to be performed.

Mounted on the same side of grip housing 20 is soak cap 27. Soak cap 27 is threadedly mounted on grip housing 20 so it can be removed conveniently when needed. Soak cap 27 covers electrical connection 26 (described below with respect to FIG. 24B) to prevent liquid contamination and to keep electrical connection 26 dry during disinfection. Often components of device 10 are submerged in a cleaning solution to disinfect components. Certain electrical components such as electrical connection 26 must be covered and isolated from the liquid to prevent damage. Soak cap 27 can be screwed over electrical connection 26 and is configured to prevent liquid intrusion and contact to connection 26. During operation of device 10, soak cap 27 is mounted on the side of housing 20 as shown in FIG. 23A for use with the disinfection of the stylet assembly 11 (FIGS. 24A-24C). Mounting soak cap 27 on grip housing 20 significantly prevents loss or misplacement of soak cap 27 when soak cap 27 is not in use. In an exemplary embodiment, soak cap 27 is made a unique and distinguishing color, such as orange to stand out from the other components. FIG. 24E illustrates cross section B-B of FIG. 24C with soak cap 27 mounted on and covering connection 26.

Detachable stylet assembly 11, as shown detached from hand grip 20 and alone in FIGS. 24A-24C and cross section views FIGS. 24D-24G, comprises an actuator housing 14. Housing 14 defines a substantially rectangular cross section and encloses an actuating assembly 15. Actuator housing 14 is mounted on and adjacent to proximal end 12A of tube 12. Actuating assembly 15 comprises a connection means 16 (FIGS. 24B and 24F) for engaging hand grip 20. Connection means 16 extends out from the enclosure of housing 14 on an opposite side from where tube 12 extends out of housing 14. Connection means 16 can be a stem that is operable to engage trigger mechanism 21 of hand grip 20. Stem 16 resembles a bullet shape and allows for mechanical engagement between the grip 20 (through linkage 32) and the articulation section 13. This engagement occurs when stylet assembly 11 is connected with hand grip 20. Actuator housing 14 includes a back plate 17 for protecting internal components of actuator assembly 15 from the external environment. Back plate 17 includes an extension 17A that lays flush with hand grip 20 when stylet 11 is attached. This provides external protection for connection means 16.

A medical professional M typically stands at the head of a patient P when intubating (shown in FIG. 1). As tube 12, with an endotracheal tube, is inserted into the trachea E of the patient P, the medical professional M can squeeze trigger 21 which is connected to actuator assembly 15 through linkage 32 and connection means 16. Actuator assembly 15 connects to a control wire 18 as shown in FIG. 24B. Control wire 18 is mounted within actuator housing 14 and connected to the connection means 16. Control wire 18 extends through tube 12 to distal end 12B and is adapted to curve the articulation section 13 upon actuation. Actuation occurs when trigger 21 is squeezed. In an exemplary embodiment, articulation section 13 is curvable via a vertebrae 213 configuration as shown in FIG. 24D or a Nitinol tube as described with respect to U.S. patent application Ser. No. 12/148,050 filed Apr. 16, 2008 incorporated hereby in its entirety. Cross section A-A of section 13 is shown in the exemplary embodiment of FIG. 24D illustrating the vertebrae 213 embodiment. Each vertebrae section 213 is adapted to allow for section 13 to curve upon actuation.

While the elongated tube 12 is preferably constructed of a rigid stainless steel tube, a polymer or other sturdy material, in some preferred embodiments can be used. The tube can be flexible or rigid. The actuating section 13 is preferably constructed of a shape memory alloy (SMA). Any shape memory alloy such as a copper-zinc-aluminum, copper-aluminum-nickel, and nickel-titanium (NiTi) alloys can be used, such as, but not limited to Nitinol. The articulation or curvable portion 13 of elongated tube 12 can be constructed of a shape memory alloy such as Nitinol with cuts to allow for articulation. The shape memory alloy (SMA) of the articulation section 13 flexes when the trigger 21 is squeezed, and then will return to its original conformation when the trigger 21 is released due to the tendency of the SMA to spring back to a less curved conformation. FIGS. 23A-23C illustrate device 10 with trigger 21 at rest and thus articulation section 13 in a substantially straight configuration.

In an exemplary embodiment, elongated tube 12 comprises at least one LED light 19 mounted adjacent the distal end 12B of elongated tube 12 as shown in FIG. 24G. LED light 19 is adapted to illuminate a pathway for stylet 10 to enter the trachea. LED light 19 is typically mounted in the tip 112 as shown in the distal tip view of FIG. 24G.

Monitor 23 can be pivotably mounted on hand grip 20 to allow for rotation to a desired viewing position. Monitor 23 can pivot towards a medical professional for better viewing. In an exemplary embodiment, the monitor can rotate or pivot approximately 180 degrees. As shown in FIGS. 23A-23C and 12-14 monitor 23 is connected to a base extension 23A which connects to hand grip 20 on pivot point 23B. Pivot point 23B can be any means for providing a desired pivot such as a screw or bolt. In a particular embodiment base extension 23A is constructed to define a substantially triangular geometry thus providing adequate support for the monitor and convenient pivoting along pivot point 23B.

Detachable stylet 11 comprises an electrical connection 26 illustrated in FIG. 24B. Electrical connection 26 extends outward from housing 14 substantially perpendicular to a longitudinal axis defined by tube 12. Connection 26 engages an electrical receiving portion of grip housing 20 to connect with monitor 23. This allows for connection to a camera having a lens 28 (shown in FIG. 24G) mounted in the tip 112. In a particular embodiment, the camera is a CMOS chip having optics. Connecting stylet 11 to handgrip 20 allows for connection of the camera to monitor 23 via electrical connection 26. The camera is connected to electrical connection 26 through one or more wires that run through the interior length of elongated tube 12. When connected or coupled to each other, monitor 23 can display a pathway through the trachea via the camera. This provides for convenient steering and guidance for the medical professional to direct the tube 12 into a desired location.

Actuator housing 14 forms an enclosure around the actuator assembly 15 and proximal end of elongated tube 12. In a particular embodiment, back plate 17 is mounted onto housing 14 by several mounting connectors 29 such as screws or bolts.

FIGS. 25A-25C and 27A illustrate an exemplary hand grip 20. Hand grip 20 comprises: (i) a grip housing 20', (ii) the trigger 21 as a pivotable lever extending from housing 20' towards distal end 12B of elongated tube 12 and away and nonparallel with respect to longitudinal axis A-A as shown in FIG. 23C; and (iii) a stationary handle 22 as base for squeezing trigger 21 towards handle 22 when engaged. Base handle 22 extends towards distal end 12B and parallel with respect to axis A-A. Trigger 21 is mounted onto housing 20' on a pivot pin 21C.

In an exemplary embodiment, trigger 21 and handle 22 each define a curving lip 21A and 22A at distal ends 21B and 22B, respectively. Lips 21A and 22A serve as terminating ends of trigger 21 and handle 22 such that a user can conveniently feel where to properly place his hand when using device 10. These lips 21A and 22A are also referred to as "stops" and typically lip 22A is substantially curved to prevent unintended hand slipping while device 10 is in use. Although shown as terminating ends, lips 21A and 22A can be located anywhere along trigger 21 and handle 22 since their intention is to provide indication to a particular hand position. Lips 21A and 22A also serve as structural stops to substantially deter slipping of the hand. Typically lips 21A and 22A face away from each other and are at substantially right angles with respect to trigger 21 and handle 22 respectively.

FIGS. 23A and 25C illustrate a side view of hand grip 20 with monitor 23 mounted thereon. In a particular embodiment, monitor 23 is mounted on a pivot mount 23A on a pivot point 23B. In a particular embodiment, a video-out port 23C is mounted on mount 23A. Typically, port 23C is an RCA composite port adapted to allow for coupling or connection to an external display means or monitor such as a computer or LCD screen. Monitor 23 further comprises a power source 23D such as a battery. Housing 20' can be securely held together by a securing means 130 such as a screw or bolt.

FIGS. 24D-24G and 26A-26D illustrate various exploded views of the internal components of both hand grip 20 and actuator assembly 15. FIGS. 26A and 27B show trigger 21 and extending lever 121 defining a cam 122 for receiving a translating pin 124. FIG. 26A is a cross section A-A of FIG. 25B. Lever 121 extends substantially perpendicular to the axis of handle 22 and defines cam 122. In an exemplary embodiment, cam 122 defines an oblong geometry to all for sliding of the lever member during squeezing, i.e. actuation, of the trigger 21. Pin 124 also connects trigger 21 to linkage 32.

Trigger 21 engages connector linkage 32 (shown alone in FIGS. 28A, 28B, and 28C) through cam 122 of lever 121 by pin 124 shown in FIG. 26A. Connector linkage 32, shown in FIG. 26A and includes a distal end 132 and a proximal end 133. The distal end connects to trigger 21 through pin 124, in pin hole 323 of linkage 32. As shown in FIG. 28A, linkage 32 includes an elongated back bone 32' that extends along a longitudinal axis B-B which is parallel with the axis of handle 22. Extending perpendicular to axis B-B are distal end 132 and proximal end 133. Back bone 32' defines an opening 233. Opening 233 defines a substantially elongated oval geometry that receives guide pin 33. As shown in FIG. 26A, guide pin 33 is mounted on the inner surface of grip housing 20' and extends through the opening 233. Pin 33 provides structural guidance to linkage 32 during actuation. Typically, when trigger 21 is squeezed towards base handle 22, lever 121 pivots to apply force to linkage 32 at the connection at distal end 132. Linkage 32 translates away from elongated tube 12. Guide pin 33 provides structural support to linkage 32 and thus backbone 32' translates along axis B-B. A coil spring 31 is positioned between proximal end 133 of linkage 32 and support stop 30. The spring is operable to return linkage 32 and thus trigger 21 back to resting position when the force on the trigger is removed.

Connection means 16 is part of actuator assembly 15. In a particular embodiment, actuator assembly 15 is constructed within actuator housing 14 of detachable stylet 11. In a further embodiment, device 10 is constructed as an entire assembly without the detachable feature. Connection means 16 can be any means to secure connection of actuator assembly 15 to linkage 32 such as a stem, protruding pin or bullet shaped extension. Connection means 16 engages a hole 334 (FIG. 28A) defined in proximal end 133 of linkage 32. Connection means 16 is attached to a plunger 34 that slides within a chamber 35 (FIGS. 24C and 24F). Chamber 35 abuts against a seal 36 to prevent liquid contamination during actuation. Plunger 34 is connected to control wire 18. During actuation, i.e., trigger 21 is being squeezed, lever 121 acts upon linkage 32 which translates away from trigger 21. As linkage 32 compresses spring 31, it acts upon connector means 16 which pulls plunger 34 to translate through chamber 35. Plunger 34 pulls control wire 18 which then causes tube 12 to curve at the articulation section 13. This mechanism provides a user with controlled curving and movement through the squeezing of trigger 21 of articulation section 13.

In an exemplary embodiment, the video signal from the monitor is broadcast wirelessly. The handle functions as a grounding plate for the dipole antenna of the wireless transmitter. The user can function as a grounding plate and thus facilitating clarity of the wireless signal to the receiver.

While the present disclosure is described herein with reference to the illustrated embodiments, it should be understood that the disclosure is not limited hereto. Those having ordinary skill in the art and access to the teachings herein will recognize additional modifications and embodiments within the scope thereof. Therefore, the present invention is limited only by the claims attached herein.

What is claimed is:

1. An endotracheal intubation device comprising:
   a handgrip including a trigger and a fixed handle, the handgrip being, adapted to detachably receive a detachable stylet assembly adapted for endotracheal intubation of a patient, intermediate the trigger and the handle;
   a linkage connected to the trigger; and
   the detachable stylet assembly being detachably received on the handgrip and including:
   (a) an elongated tube for the intubation having: a longitudinal axis, a proximal end, and a distal end for entering the trachea of the patient; wherein the elongated tube comprises (i) a rigid section adjacent the proximal end and is tubular, (ii) an articulation section adjacent the distal end and adapted to curve into the patient's trachea upon actuation, and (iii) a flexible section between the rigid section and the articulation section, the flexible section being adapted to curve freely to an internal shape of the patient's nose, nasal cavity, pharynx, and optionally larynx independently of control of the articulation section;
   (b) an actuator housing mounted on and adjacent to the proximal end of the rigid section of the elongated tube, the actuator housing comprising an actuating assembly having a connector releasably attaching the detachable stylet assembly to the hand grip and engaging the linkage connected to the trigger on the handgrip when the stylet assembly is attached to the handgrip; and
   (c) a control wire mounted within the detachable stylet and connected at a proximal end to the actuating assembly and extending to a distal end to the articulation section, wherein the control wire extends centrally through the elongated tube and is adapted to curve the articulation section upon actuation of the trigger.

2. The device of claim 1 wherein the elongated tube comprises an LED mounted adjacent the distal end of the elongated tube and adapted to illuminate a pathway for the stylet to enter the trachea.

3. The device of claim 1, wherein the elongate tube has a constant diameter and further comprising a tube stop mounted on the tube adjacent the actuator housing comprising an adjustment knob to selectively engage the constant diameter, elongate tube and adapted to allow for mounting of an endotracheal tube over and around the elongated tube.

4. The device of claim 1 wherein the actuator housing comprises an electrical connection mounted on the actuator housing and adapted to be coupled to a mating electrical connection port in the hand grip.

5. The device of claim 4 further comprising a removable soak cap adapted to be mounted on and cover the electrical connection port on the actuator housing when the stylet is being disinfected in a liquid.

6. The device of claim 4 further comprising a camera mounted adjacent the distal end of the elongate tube, and wherein the electrical connection port is coupled to the camera.

7. The device of claim 1, wherein the rigid section is directly connected to the flexible section and wherein the flexible section is directly connected to the articulated section.

8. The device of claim 1, wherein the tube has a constant diameter from the rigid section to the articulated section.

9. The device of claim 1, wherein the elongated tube defines a guide wire passage, and wherein the control wire extends through the guide wire passage and has a distal end connected to the articulation section and travels through the flexible section to curve the articulation section and not directly induce a bending at the flexible section.

10. The device of claim 1, wherein the rigid section is configured to be gripped by a hand of a person with the handgrip being held by the other hand of the person to insert the articulation section into a patient for intubation.

11. The device of claim 1, wherein the handgrip includes a display pivotable on the handgrip over 180 degrees such that the display can be viewable from adjacent the trigger to adjacent a stationary handle on an opposite side of the handgrip.

12. The device of claim 1, wherein the control wire is substantially at or near a center of the flexible section such that a tension applied to the control wire curves the articulation section but will not induce a direct bending moment to the flexible section.

13. The device of claim 12, wherein the control wire is single control wire that bends the articulation section from a rest, straight position to a forced, bent position.

14. The device of claim 13, wherein the actuator housing includes an interior and a seal to engage the connector to seal the interior of the actuator housing, and wherein the connector moves linearly in the seal to move the control wire.

15. The device of claim 14, wherein the linkage includes a proximal end arm to connect to the connector of the actuator assembly and a spring to engage the proximal end arm to urge the control wire into a position whereat the articulation section is in the rest, straight position.

16. The device of claim 1, wherein the linkage includes a protrusion, and wherein the connector includes an opening configured to receive the protrusion when the detachable stylet is connected to the handgrip.

17. The device of claim 1, wherein the handgrip includes a slot intermediate the trigger and the stationary handle and configured to receive the detachable stylet assembly, the slot being longitudinally open for the detachable stylet assembly to extend therefrom, being laterally open on a first side to receive the detachable stylet assembly, and being laterally closed on a second side at which the linkage operably attaches to the connector.

18. An endotracheal intubation device comprising:
a handgrip adapted to detachably receive a stylet assembly adapted for endotracheal intubation of a patient,
a trigger on the handgrip;
a linkage connected to the trigger; and
a stylet assembly detachably received on the handgrip and including:
  (a) an elongated tube for the intubation including: a longitudinal axis, a proximal end, and a distal end for entering the trachea of the patient; wherein the elongated tube comprises (i) a rigid section adjacent the proximal end, (ii) an articulation section adjacent the distal end and adapted to curve into the patient's trachea upon actuation, and (iii) a flexible section between the rigid section and the articulation section, the flexible section being adapted to curve to an internal shape of the patient's nose, nasal cavity, pharynx, and optionally larynx independently of control of the articulation section;
  (b) an actuator housing mounted on and adjacent to the proximal end of the rigid section of the elongated tube, the actuator housing comprising an actuating assembly having a connector releasably attaching the detachable stylet assembly to the hand grip and engaging the linkage connected to the trigger on the handgrip when the stylet assembly is attached to the handgrip; and
  (c) a control wire mounted within the detachable stylet and connected at a proximal end to the actuating assembly and connected at a distal end of the articulation section, wherein the control wire extends through the elongated tube and is adapted to curve the articulation section upon actuation of the trigger;
wherein the handgrip comprises a grip housing and a stationary handle as a base for squeezing the trigger toward the handle when engaged,
wherein the base extends towards the distal end and adjacent a proximal portion of the elongated tube,
wherein the trigger is a pivotable, elongate lever that extends from the grip housing towards the distal end of the elongated tube adjacent the proximal portion of the elongate tube and away and non-parallel with respect to the longitudinal axis;
wherein the grip housing is open laterally between the stationary handle and the trigger to receive the actuator housing therein with the stylet assembly connected to the handgrip and allow the stylet assembly to be detached from the handgrip intermediate the stationary handle and the trigger; and
wherein the flexible section includes a layered construction.

19. The device of claim 18, wherein the tube is elongate and defines a first elongate direction, wherein the trigger is elongate to define a second elongate direction and is configured to be gripped by fingers of a hand around the stationary handle with a portion of the detachable stylet intermediate the trigger, stationary handle and the hand engaging the trigger and the stationary handle, the first elongate direction is in a same direction as the second elongate direction.

20. The device of claim 18, wherein the trigger extends in a first direction along an elongate dimension of the trigger, wherein the stationary handle is elongate and extends in the first direction, and wherein the elongate tube is intermediate the trigger and the stationary handle.

21. The device of claim 20, wherein the handgrip includes a display pivotable on the handgrip over 180 degrees from adjacent the trigger to adjacent the stationary handle.

22. The device of claim 18, wherein the trigger is configured to move to a position parallel to the longitudinal axis of the tube to actuate the articulation section.

23. The device of claim 18, wherein the flexible section is freely flexible, includes a tubular structure to permit passage of the control wire therethrough near a center axis of the flexible section and is free from direct bending by the control wire.

24. The device of claim 18, wherein the flexible section includes a flexible plastic jacket, a braided tube within the flexible jacket, and a spiral-wrapped flat wire within the braided tube.

25. The device of claim 18, wherein the actuator includes a back plate that lays flush on an outer part of the handgrip and wherein the stylet assembly is detachable from the handgrip toward the back plate.

26. An endotracheal intubation device comprising:
a handgrip adapted to detachably receive a stylet assembly adapted for endotracheal intubation of a patient, the handgrip including a trigger, a linkage connected to the trigger, an elongate stationary handle; and
a stylet assembly detachably received on the handgrip positioned intermediate the trigger and the stationary handle during use and including:
  (a) an elongated tube for the intubation including: a longitudinal axis, a proximal end, and a distal end for entering the trachea of the patient; wherein the elongated tube comprises (i) a tubular, rigid section adjacent the proximal end, (ii) a tubular, articulation section adjacent the distal end and adapted to curve into the patient's trachea upon actuation, and (iii) a tubular, flexible section between the rigid section and the articulation section, the flexible section being adapted to curve to an internal shape of the patient's nose, nasal cavity, pharynx, and optionally larynx independently of control of the articulation section, and wherein the flexible section includes a layered construction;
  (b) an actuator housing mounted on and adjacent to the proximal end of the rigid section of the elongated tube, the actuator housing comprising an actuating assembly having a connector releasably attaching the detachable stylet assembly to the hand grip and engaging the linkage connected to the trigger on the handgrip when the stylet assembly is attached to the handgrip; and
  (c) a control wire centrally mounted within the detachable stylet and connected at a proximal end to the actuating assembly and connected at a distal end to the articulation section, wherein the control wire extends through the elongated tube and is adapted to curve the articulation section upon actuation of the trigger;

wherein the elongated tube comprises a camera mounted adjacent the distal end of the elongated tube, and the handgrip comprises a display means pivotably mounted on the grip housing and electrically connected to the camera.

27. The device of claim 26, wherein the trigger extends in a first direction and configured to be gripped by fingers of a hand around the stationary handle, wherein the stationary handle is elongate and extends in the first direction, wherein the elongate tube is intermediate the trigger and the stationary handle, and wherein the trigger is configured to move to a position parallel to the longitudinal axis of the tube to actuate the articulation section with a portion of the stylet assembly intermediate the trigger and the stationary handle with the hand engaged on the stationary handle and the trigger.

28. The device of claim 26, wherein the trigger includes a free end and a lip at the free end; and wherein the stationary handle is cantilevered and includes a lip at a free end.

* * * * *